(12) United States Patent
Ying et al.

(10) Patent No.: US 10,544,458 B2
(45) Date of Patent: Jan. 28, 2020

(54) DEVICE AND METHOD FOR DETECTING TARGET MOLECULES

(71) Applicant: Agency for Science, Technology and Research, Singapore (SG)

(72) Inventors: Jackie Y. Ying, Singapore (SG); Somenath Roy, Singapore (SG); Jun Hui Soh, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 8 days.

(21) Appl. No.: 15/552,021

(22) PCT Filed: Feb. 24, 2016

(86) PCT No.: PCT/SG2016/050091
§ 371 (c)(1),
(2) Date: Aug. 18, 2017

(87) PCT Pub. No.: WO2016/137398
PCT Pub. Date: Sep. 1, 2016

(65) Prior Publication Data
US 2018/0216181 A1 Aug. 2, 2018

(30) Foreign Application Priority Data
Feb. 25, 2015 (SG) .......................... 10201501398Q

(51) Int. Cl.
*C12Q 1/6876* (2018.01)
(52) U.S. Cl.
CPC .................................. *C12Q 1/6876* (2013.01)
(58) Field of Classification Search
CPC .............. C12Q 1/6876; C12N 15/1006; B01L 19/0046
See application file for complete search history.

(56) References Cited

U.S. PATENT DOCUMENTS

| | | | | |
|---|---|---|---|---|
| 7,230,092 | B2 * | 6/2007 | Bortolin | C12Q 1/6813 435/6.12 |
| 2002/0095073 | A1 * | 7/2002 | Jacobs | B01F 13/0809 600/300 |
| 2009/0280264 | A1 | 11/2009 | Laskin et al. | |
| 2014/0349287 | A1 * | 11/2014 | Liu | C12Q 1/6816 435/6.11 |

FOREIGN PATENT DOCUMENTS

| | | |
|---|---|---|
| WO | 2007035527 A2 | 3/2007 |
| WO | 2014014563 A1 | 1/2014 |

OTHER PUBLICATIONS

Pitha et al., "Poly (I-Vinyluracil): The Preparation and Interactions with Adenosine Derivatives," Biochimica et Biophysica Acta, vol. 204, 1970, pp. 39-48.

Summerton et al., "Morpholino Antisense Oligomers: Design, Preparation, and Properties," Antisense Nucleic Acid Drug Development., vol. 7, No. 3, Jun. 1997, pp. 187-195, see Abstract provided.

Stein et al., "A Specificity Comparison of Four Antisense Types: Morpholino, 2'-O-Methyl RNA, DNA, and Phosphorothioate DNA," Antisense Nucleic Acid Drug Development, vol. 7, No. 3, Jun. 1997, pp. 151-157, see Abstract provided.

Egholm et al., "Peptide Nucleic Acids (PNA). Oligonucleotide Analogues with an Achiral peptide Backbone," J. Am. Chem. Soc., vol. 114, No. 5, 1992, pp. 1895-1897.

Faruqi et al., "Peptide Nucleic Acid-Targeted Mutagenesis of a Chromosomal Gene in Mouse Cells," Proc. Natl. Acad. Sci. USA, vol. 95, Feb. 1998, pp. 1398-1403.

Christensen et al., "Solid-Phase Synthesis of Peptide Nucleic Acids," Journal of Peptide Science, vol. 1, No. 3, May-Jun. 1995, pp. 175-183, see Abstract provided.

Nielsen et al., "Peptide Nucleic Acid (PNA). A DNA Mimic with a Peptide Backbone," Bioconjugate Chem., vol. 5, 1994, pp. 3-7.

Sandhu et al., "High Efficiency Hall Effect Micro-Biosensor Platform for Detection of Magnetically Labeled Biomolecules," Biosensors and Bioelectronics, vol. 22, No. 15, 2007, pp. 2115-2123.

Li et al., "Detection of Single-Molecule DNA Hybridization Using Enzymatic Amplification in an Array of Femtoliter-Sized Reaction Vessels," J. Am. Chem. Soc., vol. 130, No. 38, Sep. 2008, pp. 12622-12623.

Jung et al., "Analysis of C-Reactive Protein on Amide-Linked N-Hydroxysuccinimide-Dextran Arrays with a Spectral Surface Plasmon Resonance Biosensor for Serodiagnosis," Analytical Chemistry, vol. 79, No. 15, Aug. 2007, pp. 5703-5710.

Sassolas et al., "DNA Biosensors and Microarrays," Chemical Reviews, vol. 108, No. 1, 2008, pp. 109-139.

Roy et al., "A Microarray Platform for Detecting Disease-Specific Circulating miRNA in Human Serum," Biosensors and Bioelectronics, vol. 75, 2016, pp. 238-246.

Extended European Search Report issued by European Patent Office for European Patent Application No. 16 755 990.5 dated Jun. 29, 2018, pp. 1-9.

Yin et al., "Electrochemcial Determination of MicroRNA-21 Based on Graphene, LNA Integrated Molecular Beacon, AuNPs and Biotin Multifunctional Bio Bar Codes and Enzymatic Assay System," Biosensors and Bioelectronics, vol. 33, 2012, pp. 247-253.

Charles et al., "Fabrication and Surface Characterization of DNA Microarrays Using Amine- and Thiol-Terminated Oligonucleotide Probes," Langmuir, vol. 19, 2003, pp. 1586-1591.

Metwalli et al., "Surface Characterizations of Mono-, Di-, and Tri-Aminosilane Treated Glass Substrates," Journal of Colloid and Interface Science, vol. 298, 2006, pp. 825-831.

(Continued)

*Primary Examiner* — Narayan K Bhat
(74) *Attorney, Agent, or Firm* — Winstead PC

(57) ABSTRACT

The present invention relates to a microarray device for detecting a target molecule such as miRNA in a sample. The device comprises a carrier substrate such as glass, an antifouling polymer layer which is functionalised with N-Hydroxysuccinimide (NHS) or carboxyl-groups and a capture probe. In an embodiment, the capture probe is an oligonucleotide with a stem-loop structure. The invention further defines a method for fabricating the device, a kit for detecting the target nucleic acid molecule comprising the device and a detection probe.

19 Claims, 5 Drawing Sheets

Specification includes a Sequence Listing.

(56) References Cited

OTHER PUBLICATIONS

Dong et al., "Trace and Label-Free Micro-RNA Detection Using Oligonucleotide Encapsulated Silver Nanoclusters as Probes," Analytical Chemistry, vol. 84, 2012, pp. 8670-8674.
Ambros, Victor, "The Functions of Animal MicroRNAs," Nature, vol. 431, Sep. 2004, pp. 350-355.
Bartel, D. P., "MicroRNAs: Genomics, Biogenesis, Mechanism, and Function," Cell, vol. 116, No. 2, Jan. 2004, pp. 281-297.
Bonnet et al., "Thermodynamic Basis of the Enhanced Specificity of Structured DNA Probes," Proc. Natl. Acad. Sci. USA, vol. 96, No. 11, May 1999, pp. 6171-6176.
Calin et al., "MicroRNA Signatures in Human Cancers," Nature Reviews Cancer, vol. 6, Nov. 2006, pp. 857-866.
Chen et al, "Characterization of MicroRNAs in Serum: A Novel Class of Biomarkers for Diagnosis of Cancer and Other Diseases," Cell Research, vol. 18, No. 10, Oct. 2008, pp. 997-1006.
Chim et al, "Detection and Characterization of Placental MicroRNAs in Maternal Plasma," Clinical Chemistry, vol. 54, 2008, pp. 482-490.
Corsten et al., "Circulating MicroRNA-208b and MicroRNA-499 Reflect Myocardial Damage in Cardiovascular Disease," Circulation Cardiovascular Genetics, vol. 3, No. 6, Oct. 2010, pp. 499-506.
De, M. et al., "Sensing of Proteins in Human Serum Using Conjugates of Nanoparticles and Green Fluorescent Protein," Nature Chemistry, vol. 1, Sep. 2009, pp. 461-465.
Diehl et al., "Digital Quantification of Mutant DNA in Cancer Patients," Current Opinion in Oncology, vol. 19, No. 1, Jan. 2007, pp. 36-42, see Abstract provided.
Ekins et al., "Development of Microspot Multi-Analyte Ratiometric Immunoassay Using Dual Fluorescent-Labelled Antibodies," Analytica Chimica Acta, vol. 227, 1989, pp. 73-96.
Esquela-Kerscher et al., "Oncomirs—MicroRNAs with a Role in Cancer," Nature Reviews Cancer, vol. 6, No. 4, Apr. 2006, pp. 259-269.
Fodor et al., "Light-Directed, Spatially Addressable Parallel Chemical Synthesis," Science, vol. 251, No. 4995, Feb. 1991, pp. 767-773.
Gilad et al., "Serum MiRNAs are Promising Novel Biomarkers," PLoS One, vol. 3, No. 9, Sep. 2008, pp. e3148-e3154.
Halliwell et al., "A Factorial Analysis of Silanization Conditions for the Immobilization of Oligonucleotides on Glass Surfaces," Analytical Chemistry, vol. 73, No. 11, Jun. 2001, pp. 2476-2483.
Hanke et al., "A Robust Methodology to Study Urine MicroRNA as Tumor Marker: MicroRNA-126 and MicroRNA-182 are Related to Urinary Bladder Cancer," Urologic Oncology, vol. 28, No. 6, Nov.-Dec. 2010, pp. 655-661, see Abstract provided.
Heneghan et al., "Circulating miRNA Signatures: Promising Prognostic Tools for Cancer," Journal of Clinical Oncology, vol. 28, No. 29, Oct. 2010, pp. 573-574.
Kloosterman et al., "The Diverse Functions of MicroRNAs in Animal Development and Disease," Developmental Cell, vol. 11, No. 4, Oct. 2006, pp. 441-450.
Ko et al., "Immobilization of Poly(ethylene glycol) or its Sulfonate onto Polymer Surfaces by Ozone Oxidation," Biomaterials, vol. 22, No. 15, 2001, pp. 2115-2123.
Lehr et al., "Real-Time Detection of Nucleic Acid Interactions by Total Internal Reflection Fluorescence," Analytical Chemistry, vol. 75, No. 10, May 2003, pp. 2414-2420.
Lewis et al., "Color-Blind Fluorescence Detection for Four-Color DNA Sequencing," Proc. Natl. Acad. Sci. USA, vol. 102, No. 15, Apr. 2005, pp. 5346-5351.
Liu et al., "Surface-Modified Poly(methyl methacrylate) Capillary Electrophoresis Microchips for Protein and Peptide Analysis," Analytical Chemistry, vol. 76, No. 23, Dec. 2004, pp. 6948-6955.
Livache et al., "Polypyrrole Based DNA Hybridization Assays: Study of Label Free Detection Processes Versus Fluorescence on Microchips," Journal of Pharmaceutical and Biomedical Analysis, vol. 32, Nos. 4-5, 2003, pp. 687-696.
Mitchell et al., "Circulating MicroRNAs as Stable Blood-Based Markers for Cancer Detection," Proc. Natl. Acad. Sci. USA, vol. 105, No. 30, Jul. 2008, pp. 10513-10518.
Oh et al., "DNA Microarrays on a Dendron-Modified Surface Improve Significantly the Detection of Single Nucleotide Variations in the p53 Gene," Nucleic Acids Research, vol. 33, No. 10, 2005, pp. e90-e97.
Riccelli et al., "Hybridization of Single-Stranded DNA Targets to Immobilized Complementary DNA Probes: Comparison of Hairpin Versus Linear Capture Probes," Nucleic Acids Research, vol. 29, No. 4, 2001, pp. 996-1004.
Rodiger et al., "Fluorescence Dye Adsorption Assay to Quantify Carboxyl Groups on the Surface of Poly(methyl methacrylate) Microbeads," Analytical Chemistry, vol. 83, No. 9, 2011, pp. 3379-3385.
Roy et al., "Mass-Produced Nanogap Sensor Arrays for Ultrasensitive Detection of DNA," J. Am. Chem. Soc., vol. 131, No. 34, Mar. 2009, pp. 12211-12217.
Roy et al., "A Microfluidic-Assisted Microarray for Ultrasensitive Detection of miRNA Under an Optical Microscope," Lab Chip, vol. 11, No. 11, 2011, pp. 1886-1894.
Sano et al., "Introduction of Functional Groups onto the Surface of Polyethylene for Protein Immobilization," Biomaterials, vol. 14, No. 11, 1993, pp. 817-822.
Sidransky, D., "Emerging Molecular Markers of Cancer," Nature Reviews Cancer, vol. 2, No. 3, Mar. 2002, pp. 210-219.
Stefani et al., "Small Non-Coding RNAs in Animal Development," Nature Reviews Molecular Cell Biology, vol. 9, Mar. 2008, pp. 219-230.
Stern et al., "Label-Free Biomarker Detection from Whole Blood," Nature Nanotechnology, vol. 5, No. 2, Feb. 2010, pp. 138-142.
Tiraferri et al., "Direct Quantification of Negatively Charged Functional Groups on Membrane Surfaces," Journal Membrane Science, vol. 389, 2012, pp. 499-508.
Tyagi et al., "Multicolor Molecular Beacons for Allele Discrimination," Nature Biotechnology, vol. 16, No. 1, Jan. 1998, pp. 49-53.
Wang et al., "Serum and Urinary Cell-Free miR-146a and miR-155 in Patients With Wystemic Lupus Erythematosus," Journal of Rheumatology, vol. 37, No. 12, Dec. 2010, pp. 2516-2522, see Abstract provided.
Watahiki et al., "MicroRNAs Associated with Metastatic Prostate Cancer," PLoS One, vol. 6, No. 9, Sep. 2011, e24950, pp. 1-13.
Weber et al., "The MicroRNA Spectrum in 12 Body Fluids," Clinical Chemistry, vol. 56, No. 11, 2010, pp. 1733-1741.
Wu et al., "Adsorption and Desorption of DNA on Graphene Oxide Studied by Fluorescently Labeled Oligonucleotides," Langmuir, vol. 27, No. 6, 2011, pp. 2731-2738.
Yang et al., "DNA-Modified Nanocrystalline Diamond Thin-Films as Stable, Biologically Active Substrates," Nature Materials, vol. 1, Dec. 2002, pp. 253-257.
Zammatteo et al., "Comparison Between Different Strategies of Covalent Attachment of DNA to Glass Surfaces to Build DNA Microarrays," Analytical Biochemistry, vol. 280, No. 1, 2000, pp. 143-150.
Zampetaki et al., "Plasma MicroRNA Profiling Reveals Loss of Endothelial miR-126 and Other MicroRNAs in Type 2 Diabetes," Circulation Research, vol. 107, No. 6, 2010, pp. 810-817.
Zhang et al., "MicroRNA-155 Contributes to Preeclampsia by Down-Regulating CYR61," American Journal of Obstetrics & Gynecology, vol. 202, May 2010, pp. 466e1-466e7, see Abstract provided.
Zhao et al., "A Pilot Study of Circulating miRNAs as Potential Biomarkers of Early Stage Breast Cancer," PLoS One, vol. 5, No. 10, Oct. 2010, pp. e13735-e13746.
Zhong et al., "Optimizing Biosensing Properties on Undecylenic Acid-Functionalized Diamond," Langmuir, vol. 23, No. 10, 2007, pp. 5824-5830.
Zu et al., "Facile and Controllable Loading of Single-Stranded DNA on Gold Nanoparticles," Analytical Chemistry, vol. 31, No. 20, Oct. 2009, pp. 8523-8528.
Chapin et al., "Ultrasensitive Multiplexed MicroRNA Quantification on Encoded Gel Microparticles Using Rolling Circle Amplification," Analytical Chemistry, vol. 83, 2011, pp. 7179-7185.

(56) References Cited

OTHER PUBLICATIONS

International Preliminary Report on Patentability for International Application No. PCT/SG2016/050091 dated Mar. 27, 2017, pp. 1-31.

* cited by examiner

DEVICE AND METHOD FOR DETECTING TARGET MOLECULES

CROSS-REFERENCE TO RELATED APPLICATION

This application makes reference to and claims the benefit of priority of the Singapore patent application no. 10201501398Q filed on Feb. 25, 2015. The content of said application is incorporated herein by reference for all purposes, including an incorporation of any element or part of the description, claims or drawings not contained herein and referred to in Rule 20.5(a) of the PCT, pursuant to Rule 4.18 of the PCT.

FIELD OF THE INVENTION

The present invention relates generally to devices and methods for detecting target molecules, especially target nucleic acid molecules.

BACKGROUND OF THE INVENTION

Nucleic acid molecules such as microRNAs (miRNAs) are targets for detection in various medical and scientific applications.

MiRNAs are a class of short (18-24 nucleotides) non-coding RNA molecules that negatively regulate gene expression at the post transcriptional level (Ambros, V. (2004). Nature, 431(7006), 350-355; Bartel, D. P. (2004). Cell, 116(2), 281-297). They play important roles in a variety of physiological and pathological processes, such as development, differentiation, cell proliferation, apoptosis, and stress responses (Kloosterman, W. P., & Plasterk; R. H. (2006). Dev Cell, 11(4), 441-450; Stefani, G., & Slack, F. J. (2008). Nat Rev Mol Cell Biol, 9, 219-230). Though miRNAs have originally emerged as cell-based biomarkers, recent reports indicated that they exist in cell-free form as well (Chim, S. S. C., et al. (2008). Clin Chem, 54, 482-490; Gilad, S., et al. (2008). PLoS One, 3(9), e3148-e3154). In fact, extra-cellular miRNAs have been detected in multiple body fluids including plasma, serum, saliva, and urine (Hanke, M., et al. (2010). Urol Oncol, 28, 655-661; Weber, J. A., et al. (2010). Clin Chem, 56(11), 1733-1741). Aberrant expression levels of such circulating miRNAs have been associated with cancer (Calin, G. A., & Croce, C. M. (2006). Nat Rev Cancer, 6, 857-866; Esquela-Kerscher, A., & Slack, F. J. (2006). Nat Rev Cancer, 6(4), 259-269; Zhao, H., et al. (2010). PLoS One, 5(10), e13735-e13746), cardiovascular disorders (Corsten, M. F., et al. (2010). Circ Cardiovasc Genet, 3(6), 499-506), abnormal pregnancies (Zhang, Y., et al. (2009). Am J Obstet Gynecol, 202, e1-7), diabetes (Zampetaki, A., et al. (2010). Circ Res, 107(6), 810-817), autoimmune diseases (Wang, G., et al. (2010). J Rheumatol, 37(12), 2516-2522), and so on. Given the facts that circulating miRNAs are highly stable (Chen, X., et al. (2008). Cell Res, 18(10), 997-1006), e.g. resistant to RNase digestion, and that their expression levels are reproducibly consistent among individuals of the same species, they show promises as novel and non-invasive biomarkers for disease detection.

With the emergence of miRNAs as key players in disease diagnosis and screening, the development of rapid, sensitive, and quantitative miRNA detection is of high interest. Chip-based devices have been used for the ultra-trace detection of analytes, and the development of a nucleic acid-based microarray is particularly useful for high-throughput detection and profiling of miRNA targets. However, the small size of miRNAs poses a major challenge toward developing a reliable assay. For a short target-probe hybrid, the oligo-nucleotide annealing temperature is low, thereby lessening the stringency of hybridization and greatly increasing the risk of false-positive signals. Selective detection of miRNA is further challenging due to high sequence homology among family members, which is as close as a single base variation. In addition, many existing technologies for RNA detection necessitate extensive sample preparation (e.g. RNA isolation, PCR amplification, tagging etc.).

Therefore, there is still need in the art for improved methods that overcome the drawbacks of existing techniques.

SUMMARY OF THE INVENTION

The present invention satisfies the aforementioned need in the art by providing a device for detecting a target molecule, a method for fabricating the device, a device fabricated by the method, a method of detecting a target nucleic acid molecule using the device as well as a kit for detecting the target nucleic acid molecule.

In a first aspect, the present invention provides a device for detecting a target molecule, the device comprising a carrier substrate, a polymer layer and a capture probe, wherein the polymer layer is immobilized on the carrier substrate and comprises a carboxyl- or N-hydroxysuccinimide (NHS)-functionalized anti-fouling polymer, and the capture probe is covalently linked to the polymer layer.

In some embodiments, the anti-fouling polymer is selected from the group consisting of polyalkylene glycol, polysaccharide such as dextran and heparin, phosphorylcholine (PC), polyglycol such as d-gluconamidoethyl methacrylate (GAMA), polyacrylate such as poly(2-methoxyethylacrylate) (PMEA), copolymers thereof, and combinations thereof.

In some embodiments, the anti-fouling polymer is polyalkylene glycol.

In some embodiments, the polyalkylene glycol is formed from monomers selected from the group consisting of ethylene glycol, propylene glycol, and combinations thereof.

In some embodiments, the polymer layer comprises or consists of carboxyl- or NHS-functionalized poly(ethylene glycol).

In some embodiments, the polymer layer is formed using a linear hetero-bifunctional poly(ethylene glycol) (PEG) comprising a carboxyl or NHS group at one end, and an amine group at the other end.

In some embodiments, the polymer layer comprises or consists of a polymer having general formula

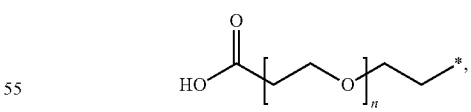

wherein n is an integer in the range of 12 to 36, and * indicates the attachment point to the carrier substrate.

In some embodiments, n is 24.

In some embodiments, the carboxyl or NHS group of the carboxyl- or NHS-functionalized anti-fouling polymer is positioned at a surface of the polymer layer.

In some embodiments, the polymer layer is a monolayer.

In some embodiments, density of carboxyl or NHS group in the polymer layer is in the range of about $5\times10^{14}$ molecules/cm$^2$ to about $5\times10^{16}$ molecules/cm$^2$.

In some embodiments, density of carboxyl or NHS group in the polymer layer is in the range of about $1 \times 10^{15}$ molecules/cm$^2$ to about $1.5 \times 10^{15}$ molecules/cm$^2$.

In some embodiments, the capture probe is covalently linked to the polymer layer by amidating the capture probe and forming a peptide bond between the amidated capture probe and the carboxyl or NHS groups of the polymer layer.

In some embodiments, the target molecule is selected from the group consisting of proteins, peptides, nucleic acids, carbohydrates, lipids, cells, viruses, small molecules, and haptens.

In some embodiments, the target molecule is detected in a body fluid comprising the target molecule.

In some embodiments, the body fluid is selected from the group consisting of plasma, serum, blood, lymph, saliva, liquor, urine, and combinations thereof.

In some embodiments, the target molecule is a target nucleic acid molecule.

In some embodiments, the capture probe is an oligonucleotide molecule comprising a nucleotide sequence having sufficient complementarity to the target nucleic acid molecule to allow formation of a capture probe-target hybrid under detection conditions.

In some embodiments, the capture probe has sufficient self-complementarity to allow formation of a stem-loop nucleic acid structure in the absence of the target nucleic acid molecule.

In some embodiments, the nucleotide sequence having sufficient complementarity to the target nucleic acid molecule to allow formation of a capture probe-target hybrid under detection conditions, is at least partially located in the loop region and its hybridization to the target nucleic acid molecule interrupts the stem-loop structure such that the capture probe adopts an open conformation.

In some embodiments, the stem region of the capture probe comprises a nucleotide sequence having sufficient complementarity to a detection probe to allow formation of a capture probe-detection probe hybrid under detection conditions and in the presence of the target nucleic acid molecule.

In some embodiments, the capture probe comprises or consists of a nucleotide sequence as set forth in SEQ ID NO:1, SEQ ID NO:3, or SEQ ID NO:7.

In some embodiments, the device comprises a plurality of capture probes.

In some embodiments, the device comprises two or more different types of capture probes for multiplexed target molecule detection.

In some embodiments, the device is a nucleic acid-based microarray.

In some embodiments, the device further comprises a linking layer arranged between the polymer layer and the carrier substrate for immobilizing the polymer layer to the carrier substrate.

In some embodiments, the linking layer comprises a homo-bifunctional linker for covalently linking the polymer layer and the carrier substrate.

In some embodiments, the homo-bifunctional linker is a dialdehyde, preferably glutaraldehyde.

In some embodiments, the target molecule is miRNA.

In some embodiments, the carrier substrate comprises or consists of a material selected from the group consisting of glass, metals, polymers, semiconductors, and combinations thereof.

In a second aspect, the invention provides a method for fabricating a device of the invention, the method comprising
a) providing a carrier substrate;
b) immobilizing a polymer layer on a surface of the carrier substrate, wherein the polymer comprises a carboxyl- or NHS-functionalized anti-fouling polymer; and
c) covalently linking a capture probe to the polymer layer.

In some embodiments, immobilizing the polymer layer comprises
a) functionalizing the carrier substrate by contacting a surface of the carrier substrate with an aminosilane to form an aminosiloxane layer on the surface of the carrier substrate;
b) contacting the aminosiloxane layer with a homo-bifunctional linker comprising two amino-reactive groups to covalently link the homo-bifunctional linker to the aminosiloxane layer to form a linking layer; and
c) contacting a carboxyl- or NHS- and amino-functionalized anti-fouling polymer with the linking layer to covalently link the carboxyl- or NHS-functionalized anti-fouling polymer to the linking layer via the amino group to obtain the polymer layer.

In some embodiments, the aminosilane comprises or consists of an aminoalkyltrialkoxysilane, preferably an aminopropyltrialkoxysilane, more preferably (3-aminopropyl)triethoxysilane (APTES).

In some embodiments, the aminosiloxane layer is a monolayer.

In some embodiments, forming an aminosiloxane layer on the carrier substrate comprises cross-linking the aminosiloxane layer.

In some embodiments, cross-linking of the aminosiloxane layer is carried out by heating the aminosiloxane layer at a temperature in the range of about 100° C. to about 150° C. for a time period in the range of about 12 hours to about 20 hours.

In some embodiments, the homo-bifunctional linker is a dialdehyde, preferably glutaraldehyde, and the reaction is carried out in the presence of a reducing agent.

In some embodiments, the reducing agent comprises or consists of NaBH$_3$CN.

In some embodiments, covalently linking a capture probe to the polymer layer comprises covalently linking a plurality of capture nucleic acid molecules to the polymer layer.

In a third aspect, the invention provides a device for detecting a target molecule fabricated by the fabrication method of the invention.

In a fourth aspect, the invention provides a method of detecting a target nucleic acid molecule, the method comprising
a) contacting a sample suspected to comprise the target nucleic acid molecule with a device of the invention or obtained by a fabrication method of the invention, wherein the capture probe has sufficient self-complementarity to allow formation of a stem-loop nucleic acid structure in the absence of the target nucleic acid molecule, under conditions that allow formation of a capture probe-target hybrid;
b) contacting a detection probe capable of hybridizing to the capture probe in the open conformation, under conditions that allow formation of a capture probe-target-detection probe hybrid; and
c) detecting presence of the capture probe-target-detection probe hybrid as indication of presence of the target nucleic acid molecule.

In some embodiments, the detection probe is an oligonucleotide molecule conjugated to a metallic nanoparticle or to a fluorescence dye.

In some embodiments, the metallic nanoparticle is a gold nanoparticle.

In some embodiments, the fluorescence dye is a polymethine dye.

In some embodiments, the detection probe comprises a sequence as recited in SEQ ID NO:5, SEQ ID NO:6, or SEQ ID NO:13.

In some embodiments, the detection probe is conjugated to a metallic nanoparticle and detecting a signal from the capture probe-target-detection probe hybrid is carried out by differential interference contrast (DIC) microscopy, dark field light-scattering and confocal microscopy, white light interferometric and confocal microscopy, or photothermal optical microscopy.

In a fifth aspect, the invention provides a kit for detecting a target nucleic acid molecule, the kit comprising
a) a device of the invention or obtained by a fabrication method of the invention; and
b) a detection probe capable of hybridizing to the capture probe in the open conformation.

In some embodiments, wherein the detection probe is an oligonucleotide molecule conjugated to a metallic nanoparticle or to a fluorescence dye.

In a final aspect, the invention encompasses use of a device of the invention or obtained by a fabrication method of the invention in a diagnostic application or in biosensing of a biomarker.

BRIEF DESCRIPTION OF THE DRAWINGS

The invention will be better understood with reference to the detailed description when considered in conjunction with the non-limiting examples and the accompanying drawings.

FIG. 5 shows selectivity and sequence mismatch discrimination study among members of the hsa-let-7 family, using hairpin and linear CPs targeting let-7a.

DETAILED DESCRIPTION OF THE INVENTION

Figure 1:
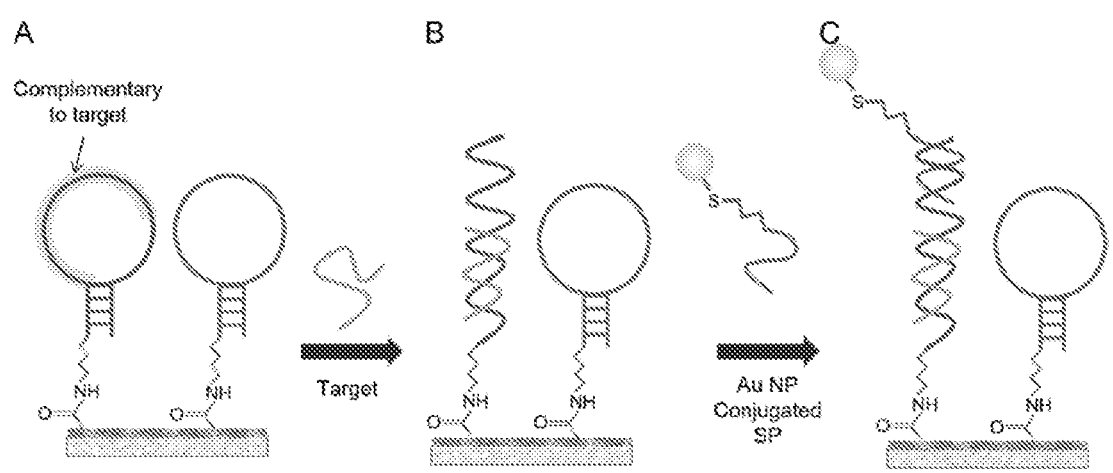
FIG. 1 shows a schematic illustration of the miRNA detection assay on a microarray, which is produced on a carboxyl-PEG functionalized glass slide. (A) Immobilization of hairpin capture probes (CPs). (B) CP-target hybridization at the loop region. (C) CP-signaling probe (SP) hybridization at the stem region.

The following detailed description refers to, by way of illustration, specific details and embodiments in which the invention may be practiced. These embodiments are described in sufficient detail to enable those skilled in the art to practice the invention. Other embodiments may be utilized and structural, and logical changes may be made without departing from the scope of the invention. The various embodiments are not necessarily mutually exclusive, as some embodiments can be combined with one or more other embodiments to form new embodiments.

Unless otherwise defined, all technical and scientific terms used herein have the same meaning as commonly understood by one of ordinary skill in the art. In case of conflict, the present document, including definitions, will control.

An object of the present invention is to provide a technique for highly sensitive and selective detection of target molecules of interest, especially target nucleic acid molecules of interest.

To this end, in a first aspect, the present invention provides a device for detecting a target molecule in a sample.

The articles "a" and "an" are used herein to refer to one or to more than one (i.e., to at least one) of the grammatical object of the article. By way of example, "an element" means at least one element and can include more than one element.

The term "device" as used herein refers to a structure, e.g. a receptacle, chamber or container or assembly of such structures, or an instrument, which allows or is suitable for the performance of molecular reactions or interactions, in particular for binding or capturing interactions as well as subsequent, related or associated molecular reactions. The device may correspondingly be equipped with one or more inlet and/or outlet elements, it may comprise one or more surfaces, e.g. reactive surfaces or surfaces with specific functionality, it may comprise one or more functional sectors, for example a reaction or binding sector, a washing sector, a mixing sector, a waiting sector, a measurement sector, a waste sector, a reservoir sector, or any sub-portion or combination thereof. It may further comprise connections between these elements, e.g. tubes or joints; and/or it may comprise reservoirs and repositories for liquids, fluids, chemicals, ingredients, samples or any other entity to be used within the device.

The term "detect" as used herein means the detection of whether or not the target molecule is present in the sample and/or the determination of the amount of the target molecule present in the sample.

The target molecule of the invention may be any entity detectable by the device of the invention. In preferred embodiments, the target molecule is a target nucleic acid molecule. The term "target nucleic acid molecule" as used herein refers to a nucleic acid molecule comprising a certain specific nucleotide sequence serving as the target of detection. It may be a nucleic acid molecule comprising a nucleotide sequence found in an animal or plant chromosome or a nucleotide sequence found in a bacterial or viral gene, or a nucleic acid molecule comprising an artificially designed nucleotide sequence. It may be a double-stranded nucleic acid, but more preferably is a single-stranded nucleic acid. It may be either DNA or RNA, for example, miRNA, siRNA, mRNA, hnRNA, genomic DNA, DNA synthesized by PCR amplification or the like, or cDNA synthesized from RNA with use of a reverse transcriptase. The length of the target nucleic acid molecule is not specifically limited, although it is preferably 10 nucleotides or longer, more preferably about 10 to 500 nucleotides, and yet more preferably about 10 to 50 nucleotides. In preferred embodiments, the target nucleic acid molecule is a miRNA.

In addition, in the present invention, the term "sample" is defined by its ordinary meaning as understood by a person skilled in the art. Examples of the sample can include a biological sample collected from an animal or the like, a sample prepared from cultured cells or the like, and a reaction solution on completion of a nucleic acid synthesis reaction. The sample may be in an intact form such as a biological sample per se, or a processed form such as a nucleic acid solution extracted and purified from a biological sample.

A device according to the present invention comprises a carrier substrate, a polymer layer and a capture probe, wherein the polymer layer is immobilized on the carrier substrate and comprises a carboxyl-functionalized anti-fouling polymer, and the capture probe is covalently linked to the polymer layer.

The term "carrier substrate" as used herein refers to any suitable substrate known to the person skilled in the art. The substrate may have any suitable form or format, e.g. it may be flat, curved, e.g. convexly or concavely curved towards, it may be curled or comprise a wavelike format. It may also be organized in round shape structures, in the form of bead-like elements, or beads, or microcarriers, which may, for example, be arranged in an array. Typically, the carrier substrate is a solid support, i.e. comprising support material, which is mainly of non-liquid consistence and thereby allows for an accurate and traceable positioning of the capture probe on the support material. Suitable carrier substrates include but are not limited to glass, metals, polymers, and semiconductors.

Immobilized on the carrier substrate is a polymer layer. The polymer layer coating may be accomplished by known methods such as dipping, spraying, or printing, and is within the knowledge of the person with average skill in the art.

The polymer layer further comprises a carboxyl- or NHS-functionalized anti-fouling polymer. As known in the art, an anti-fouling polymer acts in an anti-adhesive manner to prevent or reduce undesired interactions, such as the non-specific absorption of chemical or biochemical molecules at the substrate surface, and thus reduces undesired noise signals.

Covalently linked to the polymer layer is a capture probe designed to capture the target molecule from a sample. In preferred embodiments, the capture probe is a probe that can undergo a conformational transition upon recognizing and binding to the target molecule, whereby one portion thereof previously unreachable by a detection probe becomes accessible thereto. For detection of target nucleic acid molecules, the capture probe may comprise a single-stranded nucleic acid sequence that is complementary to a region of the target molecule and is consequently capable of forming a stable hybrid therewith under selected assay conditions and concomitantly switching from a closed conformation to an open conformation for recognition by the detection probe. In other embodiments, the capture probe may be an antibody, protein, peptide, or any other chemical entity suitable for the practice of the present invention.

The detection probe of the invention is designed according to the capture probe. For detection of a target nucleic acid molecule, the detection probe may be designed to specifically bind to the capture probe in the open conformation already hybridized with the target nucleic acid molecule, but not the capture probe in the closed conformation not binding to the target nucleic acid molecule. In preferred embodiments, the detection probe comprises an oligonucleotide capable of selectively binding to the capture probe in the open conformation under detection conditions.

In various embodiments, the detection probe is labeled with a detectable marker that can produce a signal detectable by any means. In this context, the target molecule can be determined by detecting the presence and/or amount of the signal produced by the detection probe.

In addition, one skilled in the art would readily appreciate that this design avoids the need for sample labeling and confers low background and high selectivity to the present invention. As detailed in the examples of the present application, one of the particularly advantageous characteristics of the present invention is that a single nucleotide mismatch between the target nucleic acid molecules is sufficient for a clear distinction therebetween, without the need for PCR amplification of the nucleic acid molecules.

The capture probe is complexed with the polymer layer via a molecular interaction which positions the capture probe at a specific area of the substrate surface and impedes detaching of the capture probe, e.g. during washing, rinsing or interaction steps, etc. Within the context of the present invention, the molecular interaction is based on a covalent chemical bond between the carboxyl or NHS group of the carboxyl- or NHS-thnctionalized anti-fouling polymer and the capture probe to be immobilized. For example, the capture probe to be immobilized, e.g. a nucleic acid, may comprise a functional amine group or is chemically modified in order to comprise a functional amine group. Means and methods for such a chemical modification are known to the person skilled in the art and can, for example, be derived from organic chemistry textbooks like Organische Chemie by Hart et al, 2007, Wiley-Vch or Organische Chemie by Vollhardt et al., 2005, Wiley-Vch. The localization of said functional group within the capture probe to be immobilized may be used in order to control and shape the binding behavior and/or orientation of the capture probe, e.g. the functional group may be placed at the end or tail region of the capture probe or in the center of the capture probe.

In some embodiments, the anti-fouling polymer is selected from the group consisting of polyalkylene glycol, polysaccharide such as dextran and heparin, phosphorylcholine (PC), polyglycol such as d-gluconamidoethyl methacrylate (GAMA), polyacrylate such as poly(2-methoxyethylacrylate) (PMEA), copolymers thereof, and combinations thereof.

In some embodiments, the anti-fouling polymer is polyalkylene glycol.

In some embodiments, the polyalkylene glycol is formed from monomers selected from the group consisting of ethylene glycol, propylene glycol, and combinations thereof.

In some embodiments, the polymer layer comprises or consists of carboxyl- or NHS-functionalized poly(ethylene glycol).

In some embodiments, the polymer layer is formed using a linear hetero-bifunctional poly(ethylene glycol) (PEG) comprising or consisting of a carboxyl or NHS group at one end, and an amine group at the other end.

In some embodiments, the polymer layer comprises or consists of a polymer having general formula

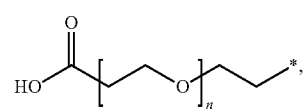

wherein n is an integer in the range of 12 to 36, and * indicates the attachment point to the carrier substrate.

In some embodiments, n is 24.

In some embodiments, the carboxyl or NHS group of the carboxyl- or NHS-functionalized anti-fouling polymer is positioned at a surface of the polymer layer.

In some embodiments, the polymer layer is a monolayer.

In some embodiments, density of carboxyl or NHS group in the polymer layer is in the range of about $5 \times 10^{14}$ molecules/cm$^2$ to about $5 \times 10^{16}$ molecules/cm$^2$.

In some embodiments, density of carboxyl or NHS group in the polymer layer is in the range of about $1 \times 10^{15}$ molecules/cm$^2$ to about $1.5 \times 10^{15}$ molecules/cm$^2$.

In some embodiments, the capture probe is covalently linked to the polymer layer by amidating the capture probe and forming a peptide bond between the amidated capture probe and the carboxyl or NHS groups of the polymer layer.

In some embodiments, the target molecule is selected from the group consisting of proteins, peptides, nucleic acids, carbohydrates, lipids, cells, viruses, small molecules, and haptens.

In some embodiments, the target molecule is detected in a body fluid comprising the target molecule.

In some embodiments, the body fluid is selected from the group consisting of plasma, serum, blood, lymph, saliva, liquor, urine, and combinations thereof.

In some embodiments, the target molecule is a target nucleic acid molecule.

In some embodiments, the capture probe is an oligonucleotide molecule comprising a nucleotide sequence having sufficient complementarity to the target nucleic acid molecule to allow formation of a capture probe-target hybrid under detection conditions.

In some embodiments, the capture probe has sufficient self-complementarity to allow formation of a stem-loop nucleic acid structure in the absence of the target nucleic acid molecule.

In some embodiments, the nucleotide sequence having sufficient complementarity to the target nucleic acid molecule to allow formation of a capture probe-target hybrid under detection conditions, is at least partially located in the loop region and its hybridization to the target nucleic acid molecule interrupts the stem-loop structure such that the capture probe adopts an open conformation.

In some embodiments, the stem region of the capture probe comprises a nucleotide sequence having sufficient complementarity to a detection probe to allow formation of a capture probe-detection probe hybrid under detection conditions and in the presence of the target nucleic acid molecule.

In accordance with the present invention, the capture probe immobilized on the surface of the carrier substrate preferably forms a stem-loop nucleic acid structure in the absence of the target nucleic acid molecule. The term "stem-loop nucleic acid structure" is used inter-changeably with "hairpin" and refers to a structure formed by an oligonucleotide comprised of 5' and 3' terminal regions that are inverted repeats and a non-self-complementary central region, wherein the self-complementary inverted repeats form a double-stranded stem and the non-self-complementary central region forms a single-stranded loop.

The present invention envisages that the stem-loop nucleic acid structure of the capture probe will, in the presence of the target nucleic acid molecule, unfold and at least part of the complementary sequence in its loop region will form a duplex with the target nucleic acid molecule in order to arrive at a more stabilized state. This unfolding will consequently expose the stem region of the stem-loop nucleic acid structure and render it accessible to a detection probe.

The capture probe and the detection probe of the present invention can be formed from natural nucleotides, chemically modified nucleotides, or nucleotide analogs. Such RNA or DNA analogs comprise, but are not limited to, 2'-O-alkyl sugar modifications, methylphosphonate, phosphorothioate, phosphorodithioate, formacetal, 3'-thioformacetal, sulfone, sulfamate, and nitroxide backbone modifications, amides, and analogs wherein the base moieties have been modified. In addition, analogs of oligomers may be polymers in which the sugar moiety has been modified or replaced by another suitable moiety, resulting in polymers which include, but are not limited to, polyvinyl backbones (Pitha et al., Biochim. Biophvs. Acta, 204:381-8 (1970); Pitha et al., Biochim. Biophvs. Acta, 204:39-48 (1970), which are hereby incorporated by reference in their entirety), morpholino backbones (Summerton, et al., Antisense Nucleic Acid Drug Dev., 7: 187-9 (1997), which is hereby incorporated by reference in its entirety) and peptide nucleic acid (PNA) analogs (Stein et al., J. Antisense Nucleic Acid Drug Dev., 7:151-7 (1997); Egholm et al., J. Am. Chem. Soc., 114 (5), pp 1895-1897 (1992); Faruqi et al., Proc. Natl. Acad. Sci. USA. 95:1398-403 (1998); Christensen et al., J. Pept. Sci., 1:175-83 (1995); Nielsen et al., Bioconjug. Chem., 5:3-7 (1994), which are hereby incorporated by reference in their entirety).

In some embodiments, the capture probe comprises or consists of a nucleotide sequence as set forth in SEQ ID NO:1, SEQ ID NO:3, or SEQ ID NO:7.

In some embodiments, the device comprises a plurality of capture probes.

In some embodiments, the device comprises two or more different types of capture probes for multiplexed target molecule detection.

In some embodiments, the device is a nucleic acid-based microarray.

The term "microarray" as used herein refers to an ordered or random array presented for interaction between the capture probes in the array and the potential interactors in the surrounding environment, e.g. a body fluid, a reaction solution, or a hybridization solution. A microarray may include any two- or three-dimensional arrangement of specific regions, preferably a two-dimensional arrangement. A microarray may contain multiple spots, features, areas of individual immobilization or areas of individual molecular identity. For example, an array may contain more than 2, 5, 10, 50, 100, 500, 750, or 1000 spots, features, capture probes or areas of individual immobilization or areas of individual molecular identity. Therefore, a plurality of target nucleic acid molecules may be simultaneously detected in a multiplexed manner.

In some embodiments, the device further comprises a linking layer arranged between the polymer layer and the carrier substrate for immobilizing the polymer layer to the carrier substrate.

In some embodiments, the linking layer comprises a homo-bifunctional linker for covalently linking the polymer layer and the carrier substrate.

In some embodiments, the homo-bifunctional linker is a dialdehyde, preferably glutaraldehyde.

In some embodiments, the target molecule is miRNA.

In some embodiments, the carrier substrate comprises or consists of a material selected from the group consisting of glass, metals, polymers, semiconductors, and combinations thereof.

In a second aspect, the invention provides a method for fabricating a device of the invention, the method comprising
a) providing a carrier substrate;
b) immobilizing a polymer layer on a surface of the carrier substrate, wherein the polymer layer comprises a carboxyl- or NHS-functionalized anti-fouling polymer; and
c) covalently linking a capture probe to the polymer layer.

In some embodiments, immobilizing the polymer layer comprises
a) functionalizing the carrier substrate by contacting a surface of the carrier substrate with an aminosilane to form an aminosiloxane layer on the surface of the carrier substrate;
b) contacting the aminosiloxane layer with a homo-bifunctional linker comprising two amino-reactive groups to covalently link the homo-bifunctional linker to the aminosiloxane layer to form a linking layer; and
c) contacting a carboxyl- or NHS- and amino-functionalized anti-fouling polymer with the linking layer to covalently link the carboxyl- or NHS-functionalized anti-fouling polymer to the linking layer via the amino group to obtain the polymer layer.

In some embodiments, the aminosilane comprises or consists of an aminoalkyltrialkoxysilane, preferably an aminopropyltrialkoxysilane, more preferably (3-aminopropyl)triethoxysilane (APTES).

In some embodiments, the aminosiloxane layer is a monolayer.

In some embodiments, forming an aminosiloxane layer on the carrier substrate comprises cross-linking the aminosiloxane layer.

In some embodiments, cross-linking of the aminosiloxane layer is carried out by heating the aminosiloxane layer at a temperature in the range of about 100° C. to about 150° C. for a time period in the range of about 12 hours to about 20 hours.

In some embodiments, the homo-bifunctional linker is a dialdehyde, preferably glutaraldehyde, and the reaction is carried out in the presence of a reducing agent.

In some embodiments, the reducing agent comprises or consists of $NaBH_3CN$.

In some embodiments, covalently linking a capture probe to the polymer layer comprises covalently linking a plurality of capture nucleic acid molecules to the polymer layer.

In a third aspect, the invention provides a device for detecting a target molecule fabricated by the fabrication method of the invention.

In a fourth aspect, the invention provides a method of detecting a target nucleic acid molecule, the method comprising
a) contacting a sample suspected to comprise the target nucleic acid molecule with a device of the invention or obtained by a fabrication method of the invention, wherein the capture probe has sufficient self-complementarity to allow formation of a stem-loop nucleic acid structure in the absence of the target nucleic acid molecule, under conditions that allow formation of a capture probe-target hybrid;
b) contacting a detection probe capable of hybridizing to the capture probe in the open conformation, under conditions that allow formation of a capture probe-target-detection probe hybrid; and
c) detecting presence of the capture probe-target-detection probe hybrid as indication of presence of the target nucleic acid molecule.

In some embodiments, the detection probe is an oligonucleotide molecule conjugated to a metallic nanoparticle or to a fluorescence dye.

In some embodiments, the metallic nanoparticle is a gold nanoparticle.

In some embodiments, the fluorescence dye is a polymethine dye.

In some embodiments, the detection probe comprises a sequence as recited in SEQ ID NO:5, SEQ ID NO:6, or SEQ ID NO:13.

In some embodiments, the detection probe is conjugated to a metallic nanoparticle and detecting a signal from the capture probe-target-detection probe hybrid is carried out by differential interference contrast (DIC) microscopy, dark field light-scattering and confocal microscopy, white light interferometric and confocal microscopy, or photothermal optical microscopy.

In a fifth aspect, the invention provides a kit for detecting a target nucleic acid molecule, the kit comprising
a) a device of the invention or obtained by a fabrication method of the invention; and
b) a detection probe capable of hybridizing to the capture probe in the open conformation.

In some embodiments, wherein the detection probe is an oligonucleotide molecule conjugated to a metallic nanoparticle or to a fluorescence dye.

In a final aspect, the invention encompasses use of a device of the invention or obtained by a fabrication method of the invention in a diagnostic application or in biosensing of a biomarker.

The present invention is further illustrated by the following examples. However, it should be understood, that the invention is not limited to the exemplified embodiments.

EXAMPLES

Materials and Methods
A. Materials and Apparatus

Plain microscope glass slides purchased from VWR International (West Chester, Pa.), with dimensions 25 mm×75 mm×1 mm, were used for surface functionalization and fabrication of microarrays. Synthetic miRNA targets, aminated oligonucleotide CPs, and thiolated oligonucleotide SPs (Table 1) were custom-made by Sigma-Aldrich (Singapore). 3-aminopropyl triethoxysilane (APTES), N-ethyl-N'-(3-dimethylaminopropyl) carbodiimide (EDC), N-hydroxysulfosuccinimide sodium salt (sulfo-NHS), Zonyl® FSN fluorosurfactant, sterile-filtered human serum and 5 M of sodium cyanoborohydride ($NaBH_3CN$) were purchased from Sigma-Aldrich (St. Louis, Mo.). Glutaraldehyde (25%) and Toluidine Blue 0 (TBO) dye were purchased from Merck KGaA (Darmstadt, Germany). Amino PEG acid, COOH—$(C_2H_4O)_{24}$—$NH_2$ (MW=1 kDa), for PEGylation of glass slides was purchased from Nanocs Inc. (New York, N.Y.). 5-nm Au NPs were obtained from BB International (Cardiff, UK). Dithiothreitol (DTT) was purchased from Gold Biotechnology, Inc.® (St. Louis, Mo.). All solutions were prepared with nuclease-free water, 20× saline sodium citrate (SSC) and 1× phosphate buffer saline (PBS), purchased from 1st Base Pte. Ltd. (Singapore).

The glass slides were treated with oxygen plasma using a CD300 gas plasma system from Europlasma NV (Oudenaarde, Belgium). Thermal curing of the glass slides was conducted in a RTP-6 infrared lamp heating system from Ulvac-Riko, Inc. (Methuen, Mass.). Microarrays were printed on functionalized glass slides using the SpotBoe 3 Personal Microarrayers (Sunnyvale, Calif.).

Table 1. Sequence information of the oligonucleotides used, bolded sequences are complementary to their respective target miRNAs, and sequences in italics are complementary to the Au NP- or Cy3-conjugated SPs.

| SEQ ID NO: | Annotation | Sequence |
|---|---|---|
| 1 | Hairpin (HPN) CP for miR-208b | 5'-NH$_2$-(CH$_2$)$_6$-TTT TTC CGC GCA CAA ACC TTT TGT TCG TCT TAT TTA ATA TAT *GCG CGG GCG*-3' |
| 2 | hsa-miR-208b | 5'-AUA AGA CGA ACA AAA GGU UUG U-3' |
| 3 | HPN CP for miR-335 | 5'-NH2-(CH2)6-TTT TTC CGC GCA CAT TTT TCG TTA TTG CTC TTG ATT AAT ATA *TGC GCG GGC G*-3' |
| 4 | hsa-miR-335 | 5'-UCA AGA GCA AUA ACG AAA AAU GU-3' |
| 5 | SP HPN-thiol | 5'-RS-S-(CH$_2$)$_6$-TTT TTT CGC CCG CGC A-3' |
| 6 | SP HPN-Cy3 | 5'-Cy3-TTT TTT CGC CCG CGC A-3' |
| 7 | HPN CP for let-7a | 5'-NH$_2$-(CH$_2$)$_6$-TTT TTC CGC GCA ACT ATA CAA CCT ACT ACC TCA TTA ATA TAT *GCG CGG GCG*-3' |
| 8 | Linear CP for let-7a | 5'- NH$_2$-(CH$_2$)$_6$-TTT TTT AAC TAT ACA ACC-3' |
| 9 | hsa-let-7a | 5'-*UGA GGU AGU AGG UUG UAU AGU U*-3' |
| 10 | hsa-let-7b | 5'-*UGA GGU AGU AGGUUGUGU GGU U*-3' |
| 11 | hsa-let-7f | 5'-*UGA GGU AGU AGA UUG UAU AGU U*-3' |
| 12 | hsa-let-7g | 5'-*UGA GGU AGU AGU UUGUAC AGU U*-3' |
| 13 | SP linear let-7a-thiol | 5'-TAC TAC CTC ATT TTT T-(CH$_2$)$_3$-S-SR-3' |

B. Functionalization of Glass Slide

Figure 2:
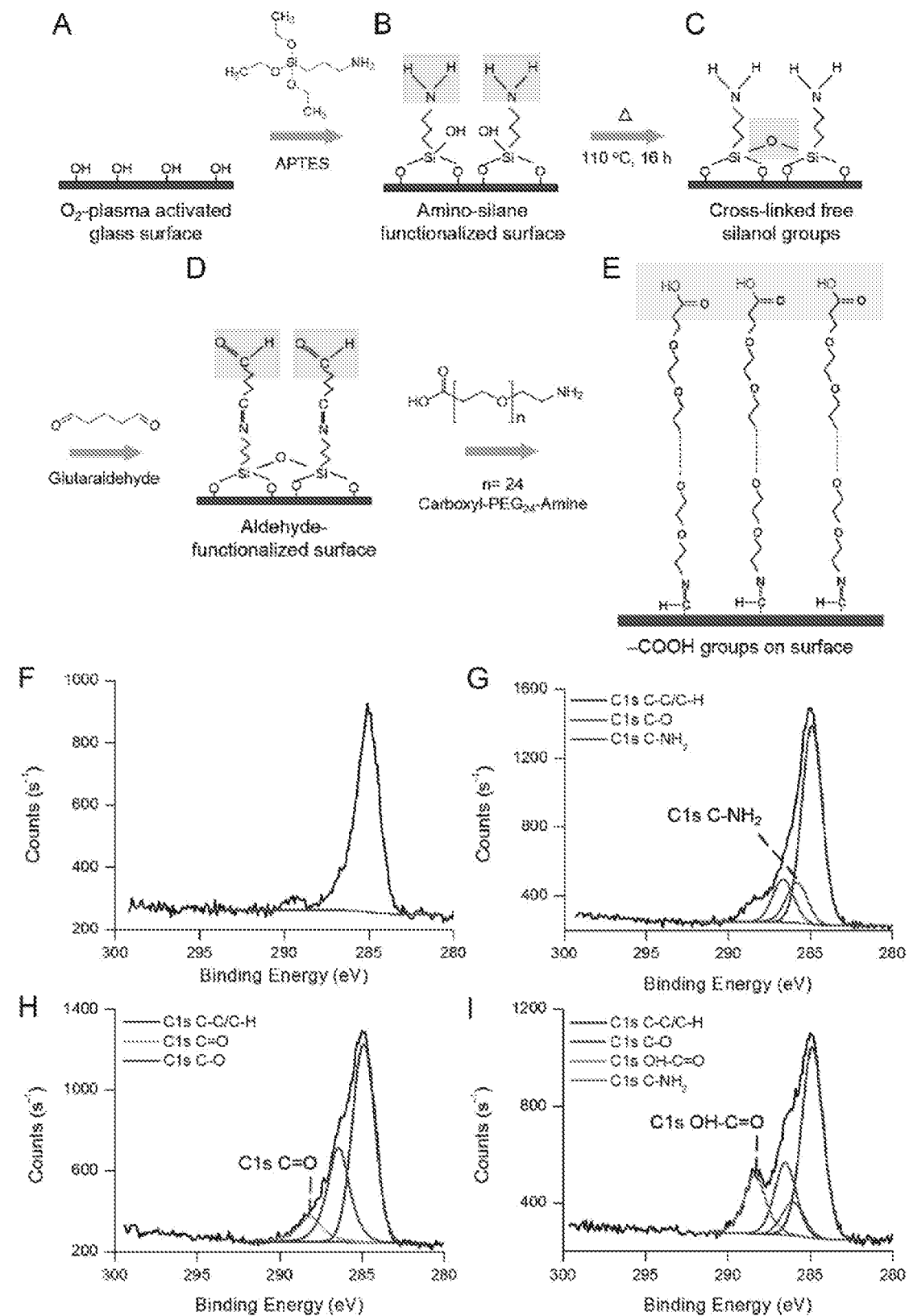
FIG. 2 shows (A-E) a schematic illustration of the procedure for the surface functionalization of glass slides and (F-I) X-ray photoelectron spectroscopy (XPS) C1s spectra of the surface functional groups on the glass slides (F) after washing with Piranha solution, (G) 3-aminopropyl triethoxysilane (APTES) coating, (H) glutaraldehyde coating, and (I) carboxyl-PEG functionalization.

The procedure for functionalizing glass slides is outlined in FIG. 2. Before functionalization, the glass slides were cleaned in Piranha solution (H$_2$SO$_4$:H$_2$O$_2$=3:1) at 120° C. for 2 h. Caution: Piranha solution is highly oxidizing, corrosive, reactive and potentially explosive, therefore, appropriate personal protective equipment (i.e. neoprene apron and face shield) should be worn at all times when handling it. Following Piranha treatment, the glass slides were rinsed thoroughly with deionized (DI) water and dried in nitrogen gas. The glass slides were then treated with oxygen plasma at 200 W for 10 min.

Subsequently, to introduce primary amine groups on the surface, the glass slides were immersed in 5% (v/v) APTES (in ethanol) solution for 2 h at room temperature with gentle shaking. They were then rinsed thoroughly with pure ethanol and dried with nitrogen. Next, the glass slides were thermally cured at 110° C. for 16 h. For addition of surface aldehyde groups, the glass slides were immersed in 4% glutaraldehyde (diluted in 1×PBS) solution containing 50 mM NaBH$_3$CN at room temperature for 2 h with gentle shaking. The slides were cleaned with 1×PBS and dried with nitrogen. Finally, to introduce a PEG layer containing surface carboxyl groups, the glass slides were immersed in 500 mM of amino-PEG-carboxylic acid (dissolved in 1×PBS) solution containing 50 mM NaBH$_3$CN at room temperature overnight with gentle shaking. After treatment with carboxyl-PEG solution, the slides were washed with 1×PBS, and dried with nitrogen.

C. Quantification of Surface Carboxyl Groups

Surface density of carboxyl groups on the glass slides was determined through evaluating the staining of basic TBO, following published procedure (Sano, S., et al. (1993). Biomaterials, 14(11), 817-822). TBO is a cationic blue dye derivative of phenothiazine (C$_{12}$H$_9$NS) (Tiraferri, A., & Elimelech, M. (2012). J Membrane Sci, 389, 499-508), which binds electrostatically to the negatively charged carboxyl group on the surface of the glass slides. The glass slides were immersed in 0.5 mM of TBO solution (pH 10, adjusted with NaOH). Complexation between TBO and the carboxyl groups was conducted at room temperature for 5 h with mild shaking. During complexation, a calibration curve was constructed, where the absorbance of TBO solutions (in 50% acetic acid) at varying concentrations were measured. Absorbance values were measured using the Infinite® M200 microplate reader (Tecan Group Ltd.). The maximum absorbance of the TBO molecules was determined to be 633 nm, and all absorbance values were taken at 633 nm.

After complexation, the glass slides appeared bluish due to staining by the TBO molecules. Subsequently, non-complexed TBO molecules were removed by washing the glass slides 3 times (5 min each) with 0.1 mM of NaOH. Finally, the glass slides were immersed in 50% acetic acid solution for desorption of complexed TBO molecules. The desorption process was conducted at room temperature for 2 h with moderate shaking to ensure all bound TBO molecules were desorbed from the surface. Aliquots of the desorption solution were collected, and their absorbance values were measured and compared to the calibration curve to determine the surface carboxyl density. A 1:1 complexation ratio between TBO and carboxyl groups was assumed during the calculation of surface carboxyl density. The quantification process was repeated for a total of 3 glass slides.

D. Immobilizing CPs on Functionalized Glass Slide for Microarray Production

In order to facilitate reaction between primary amine and carboxyl groups for the immobilization of aminated CPs, the glass slides were immersed in a solution containing 5 mM of EDC and 10 mM of sulfo-NHS (in 0.1 M of 2-(N-morpholino)ethanesulfonic acid (MES) buffer, pH 5). This activated the surface carboxyl groups for spontaneous reaction with primary amines, as EDC and sulfo-NHS would react with the carboxyl groups to form amine-reactive sulfo-NHS esters. The activation reaction was conducted at room temperature for 6 h with gentle shaking. Next, the glass slides were briefly washed with nuclease-free water and dried with nitrogen. 10 µM of aminated hairpin or linear CPs was then dissolved in 5×SSC (pH 7), and spotted in a microarray format using the SpotBot 3 microarrayer. Immobilization of the CPs was performed at room temperature overnight. Subsequently, the glass slides were washed in 5×SSC buffer and then briefly in nuclease-free water to remove unbound CPs.

E. SP-Au NP Conjugation

Conjugation of the single-stranded thiolated SP to Au NP was conducted following a published procedure (Zu, Y., & Gao, Z. (2009). Anal Chem, 81(20), 8523-8528). Briefly, 100 µM of thiolated SPs was treated with 0.1 M of DTT (dissolved in nuclease-free water) at room temperature for 2 h, and then purified using a NAP-5 column (GE Healthcare). Stock Au NP solution was first incubated with 0.05% FSN for 15 min at room temperature. Next, NaCl solution was added to achieve a final concentration of 1 M of NaCl. The solution retained its red color as the non-ionic FSN was able to stabilize the Au NPs against aggregation induced by the addition of salt (NaCl). 2 µM of thiolated SPs were then added, and the conjugation reaction was conducted at room temperature for 2 h. Thereafter, non-conjugated thiolated SPs were removed by centrifugation at 16,000 g for 15 min. The SP-Au NP conjugates were resuspended in 0.1 M of PBS (pH 7). This process was repeated 3-5 times for complete removal of non-conjugated thiolated SPs.

F. Hybridization of Target miRNA and SP on the Microarray miRNA targets of varying concentrations (1 fM-100 nM), dissolved either in 20 µl of 5×SSC buffer or in commercially obtained human serum, were applied to the immobilized CPs for CP-target hybridization. Hybridization was allowed to occur at room temperature over 4 h. The glass slides were then washed 3 times with 1×SSC buffer (1 min each) at 40° C., and with 5% ethanol (in nuclease-free water) for 30 s, with moderate shaking. After washing, the glass slides were dried in flowing nitrogen.

Next, thiolated or Cy3-labeled SPs were added to the CP target hybrid, and hybridization was allowed to occur at room temperature over 4 h. Finally, the same stringent washing steps were performed, except that they were conducted at room temperature.

G. Detection of miRNA Targets Using Optical DIC Imaging of Au NPs miRNA targets were quantified through DIC imaging of Au NPs using an Olympus IX 81 microscope, which was equipped with Nomarski prisms and a computerized stage control. Visualization of the Au NPs was done under 600× magnification with 100 ms of exposure. Estimation of the surface coverage of Au NPs was conducted using the Metamorph® software (Molecular Devices, Inc., Sunnyvale, Calif.).

H. Detection of Target Sequence Mismatch

Hairpin or linear CPs for the hsa-let-7a target (Table 1) were immobilized onto carboxyl-PEG functionalized glass slides following the procedures described earlier. Next, 100 nM of each of hsa-let-7a, hsa-let-7b, hsa-let-7f and hsa-let-7g targets (dissolved in 5×SSC buffer) was spotted onto a microarray with hairpin CPs and on another microarray with linear CPs. Subsequent SP hybridization and DIC imaging steps were conducted as described earlier. The signal intensities for the above set of miRNAs with high sequence homology were analyzed to substantiate the efficacy of the hairpin CPs in discriminating sequence mismatch over their linear counterparts.

Example 1: Assay and Mechanism for the Detection of miRNA Targets

FIG. 1 illustrates the principal steps for miRNA detection on the microarray of the invention. Specific CPs were spotted onto carboxyl-PEG functionalized glass slides by robotic spotting. Immobilization took place through covalent peptide bond formation between aminated CPs and activated carboxyl groups on the glass slide surface (FIG. 1A). The sequence complementary to the target miRNA was incorporated within the loop structure of the hairpin CP.

When the target was introduced, the hairpin structure would unfold and the complementary sequence in its loop region would form a duplex with the target miRNA (FIG. 1B). This unfolding would also expose the stem region, which contained base sequence complementary to the SP. Next, the Au NP-conjugated SPs were added, which would hybridize at the upper terminus of the already unfolded CPs (FIG. 1C). Each Au NP, representing a target miRNA-probe duplex, could be imaged under DIC microscopy. The surface coverage of Au NPs would directly correlate to the concentration of the target miRNAs in a given sample.

In the presence of a non-complementary (mismatched) target, the hairpin CP retains its stem-loop structure as the mismatched target would be unable to change its conformation, and therefore would not hybridize. Without unfolding the CP, the Au NP-tagged SP could not bind to the stem region of the hairpin, thus preventing false-positive signals (FIG. 1C). The use of a hairpin-structured CP would thus confer the detection assay with high target selectivity.

Example 2: Functionalization of Glass Slides for Anti Fouling Effect

FIG. 2 illustrates the procedure of functionalizing glass slides with carboxyl-PEG layer to achieve anti-fouling effect during detection of miRNA targets in biological fluids. Treating the glass slides with oxygen plasma (FIG. 2A) would activate silanol groups (SiOH) on the surface, promoting subsequent silanization reaction with APTES (FIG. 2B). Thermal curing of the glass slides at 110° C. for 16 h (FIG. 2C) would result in the condensation of unreacted siloxane linkages, and produce a crosslinked monolayer of APTES on the surface. This crosslinking would reduce susceptibility of the APTES monolayer to hydrolysis (Halliwell, C. M., & Cass, A. E. (2001). Anal Chem, 73(11), 2476-2483). Schiff base formation between primary amine and aldehyde would take place in the next 2 functionalization steps involving glutaraldehyde (FIG. 2D) and carboxyl-PEG (FIG. 2E). Glutaraldehyde would act as an amine-reactive homo-bifunctional crosslinker for the covalent attachment of the carboxyl-PEG layer onto the glass slide surface. Schiff base would form readily at room temperature. However, it would be labile and unstable, unless it is reduced to secondary or tertiary amines, which are highly stable and do not hydrolyze in aqueous solutions by reducing agents such as sodium borohydride ($NaBH_4$) or $NaBH_3CN$. The latter is chosen because being a milder reducing agent, it would selectively reduce Schiff base only to a secondary amine, leaving reactive aldehyde groups at the opposite end of the glutaraldehyde free to react with the carboxyl-PEG.

Elemental surface characterization of the glass slides at each stage of functionalization was conducted using X-ray photoelectron spectroscopy (XPS). The area of analysis was 400 μm×400 μm, and the depth of analysis was 5-10 nm. FIG. 2F shows the XPS C1s spectrum of a Piranha-cleaned plain glass slide without any functionalization. Addition of APTES and thermal curing yielded a XPS peak at 285.8 eV (FIG. 2G), which was attributed to the amino carbon atoms. Upon addition of glutaraldehyde, a peak emerged at 288.1 eV (FIG. 2H), which was attributed to the carbonyl carbon of aldehyde. After the addition of the carboxyl-PEG layer, a XPS peak appeared at 288.4 eV (FIG. 2I), which could be attributed to the carboxyl carbon The density and quality of surface carboxyl groups are vital for the dense immobilization of aminated CPs, and the sensitivity of miRNA targets detection. Also, signal intensity has been reported to be strongly dependent on the density of surface functional groups (Oh, S. J., et al. (2005). Nucleic Acids Res, 33(10), e90-e97). Hence, quantifying the surface carboxyl groups is vital for ensuring high assay quality. The TBO assay is utilized as it is an established dye adsorption method for surface carboxyl group quantification (Rodiger, S., et al. (2011). Anal Chem, 83(9), 3379-3385). The surface carboxyl density was determined by the TBO assay to be $1.10 (\pm 0.05) \times 10^{15}$ molecules/cm$^2$, which was consistent with the formation of a dense monolayer (Yang, W., et al. (2002). Nat Mater, 1, 253-257; Zhong, Y. L., et al. (2007). Langmuir, 23(10), 5824-5830).

Example 3: Feasibility Study

Figure 3:
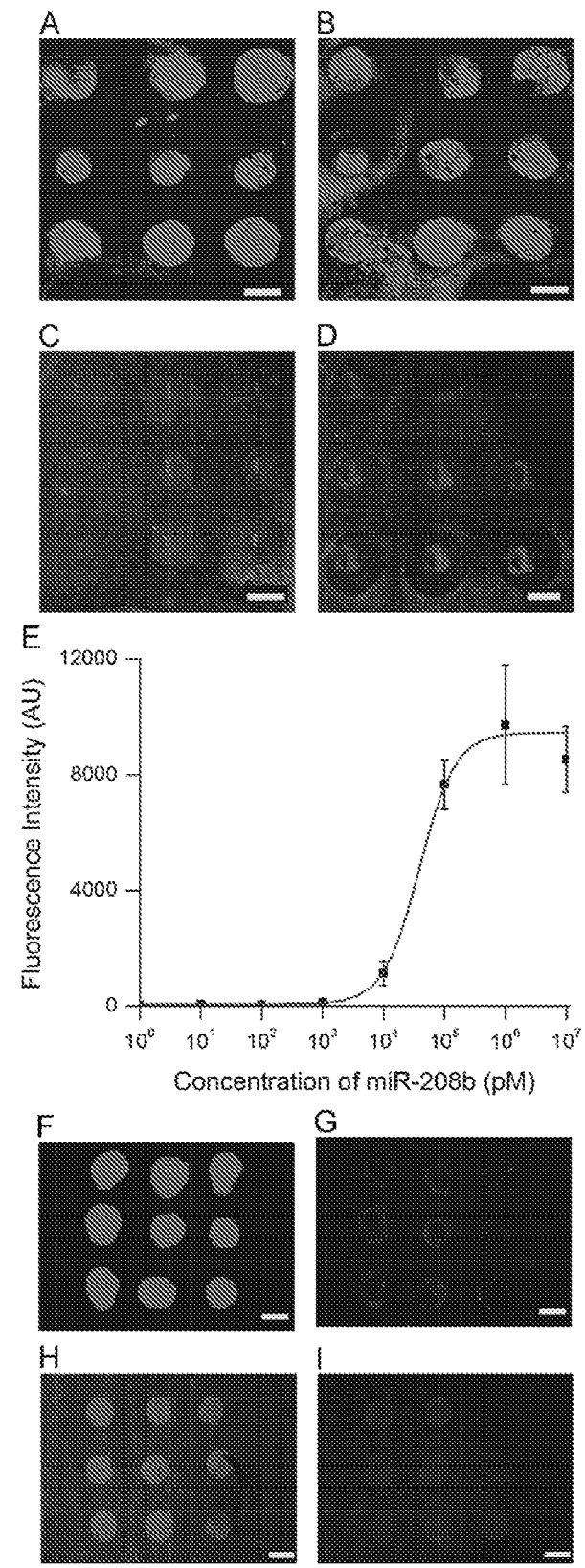
FIG. 3 shows proof-of-concept demonstration of fluorescence-based miRNA detection. Fluorescence images of on-chip hybridization between immobilized CPs and (A) 1 µM, (B) 10 nM, (C) 10 pM and (D) 100 fM of miR-208b targets. (E) Calibration curve for the fluorescence detection of miR-208b. Fluorescence images of Cy3-labeled SPs (F) immediately after spotting and (G) after stringent wash. Fluorescence images for the hybridization of Cy3-labeled SPs to immobilized hairpin CPs (H) with prior target-CP hybridization and (I) without target. Scale bars=100 µm.

Fluorescence-based nucleotide detection is the gold standard in conventional microarray analysis (Ekins, R., et al. (1989). Anal Chim Acta, 227, 73-96; Fodor, S. P., et al. (1991). Science, 251(4995), 767-773), and was therefore used as a proof-of-concept for the miRNA detection scheme shown in FIG. 1. For fluorescence-based miRNA detection, the same steps as depicted in FIG. 1 were used, except that a Cy3-conjugated SP was employed instead of a Au NP-conjugated SP. FIGS. 3A-D show the fluorescence images corresponding to decreasing concentrations of miR-208b target diluted in 5×SSC. FIG. 3E represents the calibration curve whereby the fluorescence intensities obtained from the various arrays were plotted against the miR-208b target concentrations. The concentration range investigated was 1 pM-10 μM. The calibration curve displayed a linear range over 10 nM-100 nM, and the minimum detectable concentration was 1 pM, which was consistent with other reports (Zammatteo, N., et al. (2000). Anal Biochem, 280(1), 143-150; Lehr, H. P., et al. (2003). Anal Chem, 75(10), 2414-2420; Livache, T., et al. (2003). J Pharm Biomed Anal, 32(4-5), 687-696). A direct visualization under fluorescence microscope demonstrated that the detection scheme was feasible for miRNA detection and quantification.

A couple of issues, however, remained to be addressed, namely, non-specific adsorption of SPs onto the surface of glass slides, as well as SPs hybridizing with the stem region of hairpin CPs without the presence of the target. These phenomena would give rise to false-positive results, and render the detection assay inaccurate. To determine the amount of non-specific adsorption of SPs onto the microarray surface, 1 μM of Cy3-labeled SPs was plotted onto the carboxyl-PEG surface (FIG. 3F), followed by a stringent wash. The resulting fluorescence image showed only negligible fluorescence (FIG. 3G), indicating that there was almost no non-specific adsorption of Cy3-labeled SPs onto the carboxyl-PEG surface. The carboxyl layer would deprotonate at neutral pH (under SSC conditions), producing a negative charge that would repel nucleotide molecules, which are polyanions (Wu, M., et al. (2011). Langmuir, 27(6), 2731-2738), hence reducing or eliminating non-specific adsorption of non-target nucleotide sequences.

To investigate if SPs would hybridize with the hairpin CPs even in the absence of target miRNAs, hairpin CPs were immobilized as described earlier. Next, 1 μM of Cy3-labeled SPs was applied to the immobilized hairpin CPs, and left to incubate at room temperature for 4 h. The glass slide was then washed and dried with nitrogen, and fluorescence image was taken. No or negligible fluorescence (FIG. 3I) was observed, as compared to an array added with 1 μM of perfect complementary target as positive control (FIG. 3H). Hence, it was concluded that the surface functionalization and detection schemes of the invention were able to eliminate any non-specific adsorption and false-positive results, allowing the assay to be accurate and robust.

Example 4: Detection of miRNA Targets in Buffer and Biological Fluids

Hairpin-structured CP was designed to capture miR-208b, which was chosen as the model miRNA. Plasma miR-208b levels can be used to detect patients with acute myocardial infarction (AMI), which would raise the circulating miR-208b in the plasma by 1600 folds (Corsten, M. F., et al. (2010). Circ Cardiovasc Genet, 3(6), 499-506). Once the proof-of-concept was established with the fluorophore-labeled SPs, they were replaced by their Au NP-tagged counterparts. After conducting the detection assay and hybridization steps described earlier, the amount of Au NPs was determined by DIC imaging. FIGS. 5A-C represent the DIC images of Au NPs corresponding to different miR-208b concentrations in 5×SSC buffer. The DIC imaging technique was able to create a virtual 3D morphology of individual Au NPs, allowing simple visualization and quantification of miRNA targets in an unambiguous manner (Roy, S., et al. (2009). J Am Chem Soc, 131(34), 12211-12217). The concentration range investigated was 10 fM-100 nM, and the limit of detection (LOD) was 10 fM (FIG. 4D), which was much lower as compared to that for fluorescent-based detection. In addition, the linear range was much wider (10 fM-100 nM).

Figure 4:
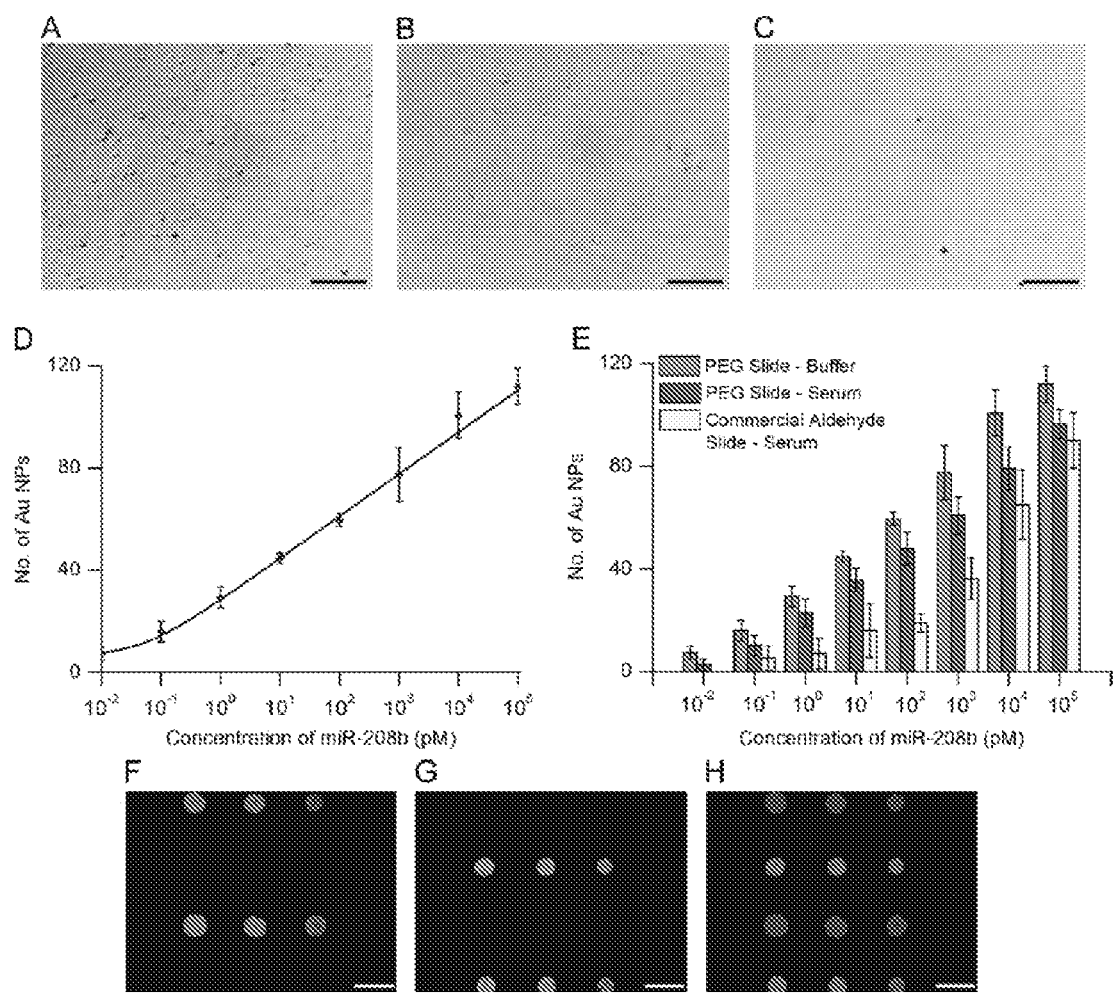
FIG. 4 shows quantification of miRNAs via DIC imaging of gold nanoparticles (Au NPs). Surface coverage of Au NPs corresponding to miR-208b target concentrations of (A) 1 nM, (B) 1 pM and (C) 1 fM, and (D) the associated calibration curve. Scale bars=50 µm. (E) Comparison of miRNA target detection in buffer and human serum on carboxyl-PEG functionalized glass slides and commercial aldehyde glass slides. Multiplexed detection study showing the hybridization of a mix of (F) miR-208b and (G) miR-335 targets to their respective hairpin CPs, and (H) the overlaid image. Scale bars=200 µm.

Since one of the principal objectives was to minimize sample preparation steps and detect circulating miRNA targets directly from biological fluids, an attempt was made to detect the concentration of cardiac disease-specific miR-208b, which was spiked into commercially available human serum. FIG. 4E compares the detection of miRNA target in 5×SSC buffer and in human serum on the carboxyl-PEG functionalized glass slide. A decrease of 22% (±7%) in signal intensity for miRNA target detection in human serum was observed, as compared to that in buffer. However, a LOD of 10 fM was still achieved for miRNA target in human serum. Additionally, the linear range of 10 fM-100 nM was retained. The LOD of 10 fM was equivalent to ~6,000 copies of miRNA/μl of sample. This fell well within the physiological abundance of plasma miRNAs, which could range from 9,000 to 134,000 copies/μl plasma (Mitchell, P. S., et al. (2008). Proc Natl Acad Sci USA, 105(30), 10513-10518), depending on the type of miRNA. Additionally, as the expression levels of many miRNAs are upregulated, e.g. miR-499 is upregulated by 100 folds for myocardial infarction (Corsten, M. F., et al. (2010). Circ Cardiovasc Genet, 3(6), 499-506) and miR-223 is increased by 55 folds for metastatic prostate cancer (Watahiki, A., et al. (2011). PLoS One, 6(9), e24950), the microarray platform of the invention can potentially be used for disease diagnosis and screening.

Furthermore, the performance of the presently disclosed carboxyl-PEG coated microarray was compared with commercial aldehyde glass slides, which do not possess an anti-fouling polymer layer (FIG. 4E). The commercial aldehyde slides were chosen as a control as they are common for printing nucleic acid microarrays. Identical procedure was followed for both types of slides as described earlier. Using the commercial aldehyde glass slide, the LOD achieved (100 fM) was 1 order of magnitude inferior to the presently disclosed carboxyl-PEG slide, and signal intensities were generally much lower, especially at lower miRNA concentrations (100 fM-1 nM). Additionally, the linear range was reduced to ~100 pM-100 nM. Hence, the carboxyl-PEG coated microarray disclosed herein outperformed the commercial aldehyde slide in detection of miRNA target in human serum. The protein-resistant property of PEG (Ko, Y. G., et al. (2001). Biomaterials, 22(15), 2115-2123; Liu, J., et al. (2004). Anal Chem, 76(23), 6948-6955) has enabled the carboxyl-PEG microarray of the invention to sensitively detect target miRNA directly from biological fluids without extensive sample preparation steps.

To demonstrate the multiplexing capabilities of the microarray platform, 10 µM of hairpin CPs for miR-208b (1st and 3rd rows) and miR-335 (2nd and 4th rows) (FIG. 4F-H) were immobilized onto the carboxyl-PEG functionalized glass slide. Next, a solution containing 100 nM of Cy3-labeled miR-208b and 100 nM of FAM-labeled miR-335 targets was added to the array of CPs. Hybridization was allowed to occur at room temperature for 4 h, followed by stringent washes. The targets only hybridized to their respective capture probes as Cy3 fluorescence was only seen on the 1st and 3rd rows and FAM fluorescence was only observed on the 2nd and 4th rows. Also, there was virtually no cross-contamination, thus the immobilized CPs were very selective for their individual targets. The throughput could be easily scaled up for DIC imaging of Au NPs through spatial mapping of different CPs on the glass slide and software analysis of the images. This would allow for high-throughput miRNA quantification and profiling.

Example 5: Discriminating Sequence Mismatches Using Hairpin and Linear CPs

Figure 5:
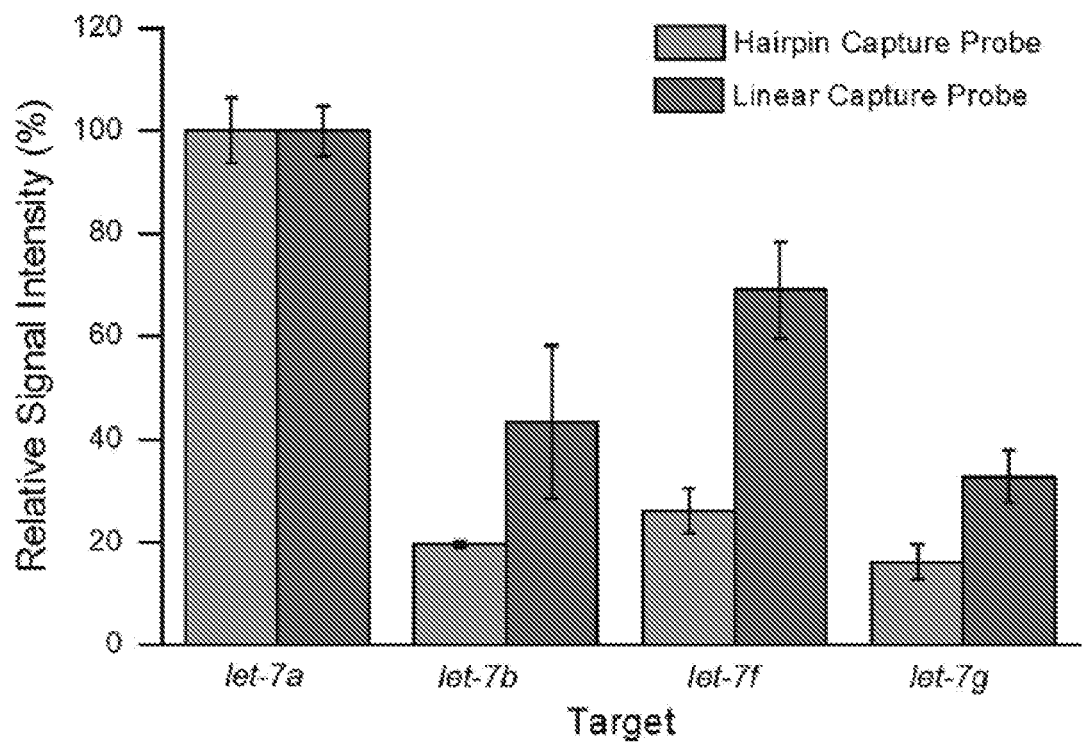

Members within a specific miRNA family often differ in sequence by only a single base. Hence, for an accurate analysis of miRNA expression profiles, it is important for detection assays to discriminate sequence mismatches with high accuracy. Additionally, many human diseases, such as cancer, occur due to point mutations in one or more genes (Sidransky, D. (2002). Nat Rev Cancer, 2(3), 210-219), and such mutations can be used as important molecular markers to detect early-stage tumorigenesis (Diehl, F., & Diaz, L. A. J. (2007). Curr Opin Oncol, 19, 36-42). For the sequence mismatch discrimination study, 4 members were selected from the hsa-let-7 family, namely let-7a, let-7b, let-7f and let-7g, which have high sequence homology. Hairpin and linear CPs were designed in such a way that let-7a target was the perfect match (PM) for each of them. There is a single-base mismatch (1 MM) between let-7a and let-7f and a two-base mismatch (2 MM) between let-7a and let-7b, as well as between let-7a and let-7g (Table 1). FIG. 5 shows that when hairpin CP for let-7a was used, there is a 74% drop in signal intensity for let-7f (1 MM), and an even greater decrease (~80% and 84% respectively) for let-7b and let-7g (2 MM), as compared to let-7a (PM). For let-7b, the two-base mismatch involves two A-T bonds, whereas that for let-7g involves one A-T and one C-G bond. Since a C-G pair is connected by three hydrogen bonds while an A-T pair involves two, the resulting decrease in melting temperature for base mismatch was greater for let-7g than for let-7b. As a consequence, a greater decrease in signal intensity was observed for let-7g compared to let-7b, even though both targets contained two-base mismatch as compared to let-7a.

On the other hand, for a linear CP complementary to let-7a, a smaller extent of decrease was observed in signal intensities. There is a ~31% drop in signal intensity for let-7f (1 MM), and a decrease of ~57% and 67%, respectively, for let-7b and let-7g (2 MM), as compared to let-7a (PM). Due to their stem-loop structure, hairpin CPs are constrained molecules, therefore upon formation or dissociation of CP-target complex, they experience a greater structural reorganization as compared to linear CPs (Bonnet, G., et al. (1999). Proc Natl Acad Sci USA, 96(11), 6171-6176). This has enabled their increased sensitivity and ability to discriminate sequence mismatch. Furthermore, it has been reported that hairpin CPs demonstrate higher hybridization rates and that hairpin CP-target complexes are more stable than their linear counterparts (Riccelli, P. V., et al. (2001). Nucleic Acids Res, 29(4), 996-1004). These properties offer substantial advantages, especially in a point-of-care (POC) setting, which requires rapid and sensitive signal readout for diagnostic purposes.

In summary, exemplified herein is a microrray platform developed for highly sensitive and selective detection of disease-specific circulating miRNAs with miR-208b as a model marker for cardiac disease. To the knowledge of the inventors of the present invention, it was the first demonstration of a microarray-based technique that is capable of direct profiling of miRNA targets from body fluids, such as human serum. The platform was able to detect as low as 10 fM (equivalent to ~6000 copies in a microliter sample) of target miRNAs in human serum, without the need for further sample processing and labeling or PCR amplification. Application of carboxyl-PEG functional layer on the microarray surface and exploitation of hairpin CPs enabled such outstanding performance. The carboxyl-PEG functionalized microarray disclosed herein was superior to the commercial aldehyde slides in the detection of miRNA targets in human serum, thus highlighting the importance of anti-fouling treatment for reducing interference from complex biological media. On a single microarray, multiple targets could be detected with negligible cross-contamination, showing the potential for multiplexed assay. Furthermore, the microarray could discriminate between the members of a miRNA family with a high sequence homology. With all the aforementioned capabilities, the microarray platform is well suited for various applications, including but not limited to rapid and non-invasive profiling and quantification of circulating miRNAs in serum and plasma samples for POC diagnostic purposes.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. Other embodiments are within the following claims. In addition, where features or aspects of the invention are described in terms of Mannish groups, those skilled in the art will recognize that the invention is also thereby described in terms of any individual member or subgroup of members of the Markush group.

One skilled in the art would readily appreciate that the present invention is well adapted to carry out the objects and obtain the ends and advantages mentioned, as well as those inherent therein. Further, it will be readily apparent to one skilled in the art that varying substitutions and modifications may be made to the invention disclosed herein without departing from the scope and spirit of the invention. The compositions, methods, procedures, treatments, molecules and specific compounds described herein are presently representative of preferred embodiments are exemplary and are not intended as limitations on the scope of the invention. Changes therein and other uses will occur to those skilled in the art which are encompassed within the spirit of the invention are defined by the scope of the claims. The listing or discussion of a previously published document in this specification should not necessarily be taken as an acknowledgement that the document is part of the state of the art or is common general knowledge.

The invention illustratively described herein may suitably be practiced in the absence of any element or elements, limitation or limitations, not specifically disclosed herein. Thus, for example, the terms "comprising", "including," containing", etc. shall be read expansively and without limitation. The word "comprise" or variations such as "comprises" or "comprising" will accordingly be understood to imply the inclusion of a stated integer or groups of integers but not the exclusion of any other integer or group of integers. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by exemplary embodiments and optional features, modification and variation of the inventions embodied therein herein disclosed may be resorted to by those skilled in the art, and that such modifications and variations are considered to be within the scope of this invention.

The content of all documents and patent documents cited herein is incorporated by reference in their entirety.

What is claimed is:

1. A nucleic acid-based microarray for detecting a target nucleic acid molecule in a sample, wherein the target nucleic acid molecule is miRNA, the microarray comprising a carrier substrate, a polymer layer and a capture probe, wherein the polymer layer is immobilized on the carrier substrate and comprises a carboxyl- or N-hydroxysuccinimide (NHS)-functionalized anti-fouling polymer, a linking layer arranged between the polymer layer and the carrier substrate for immobilizing the polymer layer to the carrier substrate, with the linking layer comprising a dialdehyde linker for covalently linking the polymer layer and the carrier substrate, and the capture probe is covalently linked to the polymer layer, wherein the capture probe is an oligonucleotide molecule comprising a nucleotide sequence having sufficient complementarity to the target nucleic acid molecule to allow formation of a capture probe-target hybrid under detection conditions, wherein the capture probe has sufficient self-complementarity to allow formation of a stem-loop nucleic acid structure in the absence of the target nucleic acid molecule, wherein the nucleotide sequence of the capture probe having sufficient complementarity to the target nucleic acid molecule to allow formation of a capture probe-target hybrid under detection conditions is at least partially located in the loop region and its hybridization to the target nucleic acid molecule interrupts the stem-loop structure such that the capture probe adopts an open conformation, wherein the stem region of the capture probe comprises a nucleotide sequence having sufficient complementarity to a detection probe to allow formation of a capture probe-detection probe hybrid under detection conditions and in the presence of the target nucleic acid molecule.

2. The microarray according to claim 1, wherein:
 (a) the anti-fouling polymer is selected from the group consisting of polyalkylene glycol, polysaccharides comprising dextran and heparin, phosphorylcholine (PC), polyglycols comprising d-gluconamidoethyl methacrylate (GAMA), polyacrylates comprising poly (2-methoxyethylacrylate) (PMEA), copolymers thereof, and combinations thereof; or
 (b) the anti-fouling polymer is polyalkylene glycol optionally formed from monomers selected from the group consisting of ethylene glycol, propylene glycol, and combinations thereof.

3. The microarray according to claim 1, wherein:
 (a) the polymer layer comprises or consists of carboxyl- or NETS-functionalized poly(ethylene glycol); or
 (b) the polymer layer is formed using a linear heterobifunctional poly(ethylene glycol) (PEG) comprising or consisting of a carboxyl or NHS group at one end, and an amine group at the other end; or
 (c) the polymer layer comprises or consists of a polymer having general formula

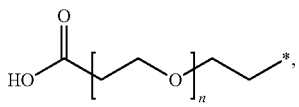

wherein n is an integer in the range of 12 to 36, optionally 24, and * indicates the attachment point to the carrier substrate; or (d) the polymer layer is a monolayer.

4. The microarray according to claim 1, wherein: a density of carboxyl or NHS group in the polymer layer is in the range of about $5 \times 10^{14}$ molecules/cm$^2$ to about $5 \times 10^{16}$ molecules/cm$^2$.

5. The microarray according to claim 1, wherein the capture probe is covalently linked to the polymer layer by aminating the capture probe and forming a peptide bond between the aminated capture probe and the carboxyl or NHS groups of the polymer layer.

6. The microarray according to claim 1, wherein the target molecule is detected in a body fluid comprising the target molecule, with the body fluid being optionally selected from the group consisting of plasma, serum, blood, lymph, saliva, liquor, urine, and combinations thereof.

7. The microarray according to claim 1, wherein the capture probe comprises or consists of a nucleotide sequence as set forth in SEQ ID NO:1, SEQ ID NO:3, or SEQ ID NO:7.

8. The microarray according to claim 1, wherein the microarray comprises a plurality of capture probes.

9. The microarray according to claim 1, wherein the microarray comprises two or more different types of capture probes for multiplexed target molecule detection.

10. The microarray according to claim 1, wherein the carrier substrate comprises or consists of a material selected from the group consisting of glass, metals, polymers, semiconductors, and combinations thereof.

11. A method for fabricating a microarray for detecting a target nucleic acid molecule in a sample, wherein the target nucleic acid molecule is miRNA, the microarray comprising a carrier substrate, a polymer layer and a capture probe, wherein the polymer layer is immobilized on the carrier substrate and comprises a carboxyl- or N-hydroxysuccinimide (NHS)-functionalized anti-fouling polymer, a linking layer arranged between the polymer layer and the carrier substrate for immobilizing the polymer layer to the carrier substrate, and the capture probe is covalently linked to the polymer layer, wherein the capture probe is an oligonucleotide molecule comprising a nucleotide sequence having sufficient complementarity to the target nucleic acid molecule to allow formation of a capture probe-target hybrid under detection conditions, wherein the capture probe has sufficient self-complementarity to allow formation of a stem-loop nucleic acid structure in the absence of the target nucleic acid molecule, wherein the nucleotide sequence of the capture probe having sufficient complementarity to the target nucleic acid molecule to allow formation of a capture probe-target hybrid under detection conditions is at least partially located in the loop region and its hybridization to the target nucleic acid molecule interrupts the stem-loop structure such that the capture probe adopts an open conformation, wherein the stem region of the capture probe comprises a nucleotide sequence having sufficient complementarity to a detection probe to allow formation of a capture probe-detection probe hybrid under detection conditions and in the presence of the target nucleic acid molecule, wherein the target nucleic acid molecule is miRNA, the method comprising a) providing a carrier substrate;
b) immobilizing a polymer layer on a surface of the carrier substrate, wherein the polymer layer comprises a carboxyl- or NHS-functionalized anti-fouling polymer; and
c) covalently linking a capture probe to the polymer layer, wherein immobilizing the polymer layer comprises
a) functionalizing the carrier substrate by contacting a surface of the carrier substrate with an aminosilane to form an aminosiloxane layer on the surface of the carrier substrate;
b) contacting the aminosiloxane layer with a dialdehyde linker comprising two amino-reactive groups to covalently link the dialdehyde linker to the aminosiloxane layer to form the linking layer; and
c) contacting a carboxyl- or NETS- and amino-functionalized anti-fouling polymer with the linking layer to covalently link the carboxyl- or NETS-functionalized anti-fouling polymer to the linking layer via the amino group to obtain the polymer layer.

12. The method according to claim 11, wherein the aminosilane comprises or consists of an aminoalkyltrialkoxysilane, preferably an aminopropyltrialkoxysilane, more preferably (3-aminopropyl)triethoxysilane (APTES).

13. The method according to claim 11, wherein the aminosiloxane layer is a monolayer.

14. The method according to claim 11, wherein forming an aminosiloxane layer on the carrier substrate comprises cross-linking the aminosiloxane layer.

15. The method according to claim 11, wherein cross-linking of the aminosiloxane layer is carried out by heating the aminosiloxane layer at a temperature in the range of about 100° C. to about 150° C. for a time period in the range of about 12 hours to about 20 hours.

16. The method according to claim 11, wherein the dialdehyde linker is glutaraldehyde, and the reaction is carried out in the presence of a reducing agent, with the reducing agent comprising or consisting of $NaBH_3CN$.

17. The method according to claim 11, wherein covalently linking a capture probe to the polymer layer comprises covalently linking a plurality of capture nucleic acid molecules to the polymer layer.

18. A method of detecting a target nucleic acid molecule, wherein the target nucleic acid molecule is miRNA, the method comprising a) contacting a sample suspected to comprise the target nucleic acid molecule with a microarray, wherein the capture probe has sufficient self-complementarity to allow formation of a stem-loop nucleic acid structure in the absence of the target nucleic acid molecule, under conditions that allow formation of a capture probe-target hybrid;
b) contacting a detection probe capable of hybridizing to the capture probe in the open conformation, under conditions that allow formation of a capture probe-target-detection probe hybrid; and
c) detecting presence of the capture probe-target-detection probe hybrid as indication of presence of the target nucleic acid molecule, wherein the microarray:
(A) comprises a carrier substrate, a polymer layer and a capture probe, wherein the polymer layer is immobilized on the carrier substrate and comprises a carboxyl- or N-hydroxysuccinimide (NHS)-functionalized anti-fouling polymer, a linking layer arranged between the polymer layer and the carrier substrate for immobilizing the polymer layer to the carrier substrate, and the capture probe is covalently linked to the polymer layer, wherein the capture probe is an oligonucleotide molecule comprising a nucleotide sequence having sufficient complementarity to the target nucleic acid molecule to allow formation of a capture probe-target hybrid under detection conditions, wherein the capture probe has sufficient self-complementarity to allow formation of a stem-loop nucleic acid structure in the absence of the target nucleic acid molecule, wherein the nucleotide sequence of the capture probe having sufficient complementarity to the target nucleic acid molecule to allow formation of a capture probe-target hybrid under detection conditions is at least partially located in the loop region and its hybridization to the target nucleic acid molecule interrupts the stem-loop structure such that the capture probe adopts an open conformation, wherein the stem region of the capture probe comprises a nucleotide sequence having sufficient complementarity to a detection probe to allow formation of a capture probe-detection probe hybrid under detection conditions and in the presence of the target nucleic acid molecule; or (B) is obtained by a method for fabricating a microarray for detecting a target nucleic acid molecule, the method comprising
   a) providing a carrier substrate;
   b) immobilizing a polymer layer on a surface of the carrier substrate, wherein the polymer layer comprises a carboxyl- or NHS-functionalized anti-fouling polymer; and
   c) covalently linking a capture probe to the polymer layer,
wherein immobilizing the polymer layer comprises
   a) functionalizing the carrier substrate by contacting a surface of the carrier substrate with an aminosilane to form an aminosiloxane layer on the surface of the carrier substrate;
   b) contacting the aminosiloxane layer with a dialdehyde linker comprising two amino-reactive groups to covalently link the dialdehyde linker to the aminosiloxane layer to form the linking layer; and
   c) contacting a carboxyl- or NETS- and amino-functionalized anti-fouling polymer with the linking layer to covalently link the carboxyl- or NHS-functionalized anti-fouling polymer to the linking layer via the amino group to obtain the polymer layer,
wherein the detection probe is an oligonucleotide molecule conjugated to a metallic nanoparticle or to a fluorescence dye.

19. The method according to claim 18, wherein the metallic nanoparticle is a gold nanoparticle, or wherein the fluorescence dye is a polymethine dye, or wherein the detection probe comprises a sequence as recited in SEQ ID NO:5, SEQ ID NO:6, or SEQ ID NO:13, or wherein the detection probe is conjugated to a metallic nanoparticle and detecting a signal from the capture probe-target-detection probe hybrid is carried out by differential interference contrast (DIC) microscopy, dark field light-scattering and confocal microscopy, white light interferometric and confocal microscopy, or photothermal optical microscopy.

* * * * *

SEQUENCE LISTING

```
<160> NUMBER OF SEQ ID NOS: 13

<210> SEQ ID NO 1
<211> LENGTH: 51
<212> TYPE: DNA
<213> ORGANISM: Artificial Sequence
<220> FEATURE:
<223> OTHER INFORMATION: Synthesized
<220> FEATURE:
<221> NAME/KEY: modified_base
<222> LOCATION: (1)..(1)
<223> OTHER INFORMATION: Modified by -NH2-(CH2)6-.

<400> SEQUENCE: 1
tttttccgcg cacaaacctt tgttcgtct tatttaatat atgcgcgggc g        51

<210> SEQ ID NO 2
<211> LENGTH: 22
<212> TYPE: RNA
<213> ORGANISM: Homo sapiens

<400> SEQUENCE: 2
auaagacgaa caaaagguuu gu                                       22

<210> SEQ ID NO 3
<211> LENGTH: 52
<212> TYPE: DNA
<213> ORGANISM: Artificial Sequence
<220> FEATURE:
<223> OTHER INFORMATION: Synthesized
<220> FEATURE:
<221> NAME/KEY: modified_base
<222> LOCATION: (1)..(1)
<223> OTHER INFORMATION: Modified by -NH2-(CH2)6-.

<400> SEQUENCE: 3
tttttccgcg cacatttttc gttattgctc ttgattaata tatgcgcggg cg       52

<210> SEQ ID NO 4
<211> LENGTH: 23
<212> TYPE: RNA
<213> ORGANISM: Homo sapiens
```

```
<400> SEQUENCE: 4
ucaagagcaa uaacgaaaaa ugu                                          23

<210> SEQ ID NO 5
<211> LENGTH: 16
<212> TYPE: DNA
<213> ORGANISM: Artificial Sequence
<220> FEATURE:
<223> OTHER INFORMATION: Synthesized
<220> FEATURE:
<221> NAME/KEY: modified_base
<222> LOCATION: (1)..(1)
<223> OTHER INFORMATION: Modified by -RS-S-(CH2)6-.

<400> SEQUENCE: 5 tttttcgcc cgcgca                                                   16

<210> SEQ ID NO 6
<211> LENGTH: 16
<212> TYPE: DNA
<213> ORGANISM: Artificial Sequence
<220> FEATURE:
<223> OTHER INFORMATION: Synthesized
<220> FEATURE:
<221> NAME/KEY: modified_base
<222> LOCATION: (1)..(1)
<223> OTHER INFORMATION: Modified by -Cy3-.

<400> SEQUENCE: 6 tttttcgcc cgcgca                                                   16

<210> SEQ ID NO 7
<211> LENGTH: 51
<212> TYPE: DNA
<213> ORGANISM: Artificial Sequence
<220> FEATURE:
<223> OTHER INFORMATION: Synthesized
<220> FEATURE:
<221> NAME/KEY: modified_base
<222> LOCATION: (1)..(1)
<223> OTHER INFORMATION: Modified by -NH2-(CH2)6-.

<400> SEQUENCE: 7
tttttccgcg caactataca acctactacc tcattaatat atgcgcgggc g            51

<210> SEQ ID NO 8
<211> LENGTH: 18
<212> TYPE: DNA
<213> ORGANISM: Artificial Sequence
<220> FEATURE:
<223> OTHER INFORMATION: Synthesized
<220> FEATURE:
<221> NAME/KEY: modified_base
<222> LOCATION: (1)..(1)
<223> OTHER INFORMATION: Modified by -NH2-(CH2)6-.

<400> SEQUENCE: 8 tttttttaact atacaacc                                               18

<210> SEQ ID NO 9
<211> LENGTH: 22
<212> TYPE: RNA
<213> ORGANISM: Homo sapiens

<400> SEQUENCE: 9
ugagguagua gguuguauag uu                                           22
```

```
<210> SEQ ID NO 10
<211> LENGTH: 22
<212> TYPE: RNA
<213> ORGANISM: Homo sapiens

<400> SEQUENCE: 10
ugagguagua gguugugugg uu                                              22

<210> SEQ ID NO 11
<211> LENGTH: 22
<212> TYPE: RNA
<213> ORGANISM: Homo sapiens

<400> SEQUENCE: 11
ugagguagua gauuguauag uu                                              22

<210> SEQ ID NO 12
<211> LENGTH: 22
<212> TYPE: RNA
<213> ORGANISM: Homo sapiens

<400> SEQUENCE: 12
ugagguagua guuuguacag uu                                              22

<210> SEQ ID NO 13
<211> LENGTH: 16
<212> TYPE: DNA
<213> ORGANISM: Artificial Sequence
<220> FEATURE:
<223> OTHER INFORMATION: Synthesized
<220> FEATURE:
<221> NAME/KEY: modified_base
<222> LOCATION: (16)..(16)
<223> OTHER INFORMATION: Modified by -(CH2)3-S-SR-.

<400> SEQUENCE: 13
tactacctca tttttt                                                     16
```